(12) United States Patent
Yang et al.

(10) Patent No.: US 11,795,444 B2
(45) Date of Patent: Oct. 24, 2023

(54) COMPOSITION FOR PRODUCING TAGATOSE AND METHOD OF PRODUCING TAGATOSE USING THE SAME

(71) Applicant: CJ CheilJedang Corporation, Seoul (KR)

(72) Inventors: Sung Jae Yang, Suwon-si (KR); Hyun Kug Cho, Suwon-si (KR); Young Mi Lee, Suwon-si (KR); Seong Bo Kim, Seongnam-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 662 days.

(21) Appl. No.: 16/499,223

(22) PCT Filed: Mar. 30, 2018

(86) PCT No.: PCT/KR2018/003749
§ 371 (c)(1),
(2) Date: Sep. 27, 2019

(87) PCT Pub. No.: WO2018/182345
PCT Pub. Date: Oct. 4, 2018

(65) Prior Publication Data
US 2022/0177936 A1    Jun. 9, 2022

(30) Foreign Application Priority Data
Mar. 31, 2017 (KR) .................. 10-2017-0042165

(51) Int. Cl.
| | | |
|---|---|---|
| C12N 9/88 | (2006.01) | |
| C12N 9/12 | (2006.01) | |
| C12N 9/90 | (2006.01) | |
| C12P 19/02 | (2006.01) | |
| C12P 19/24 | (2006.01) | |
| C12N 9/10 | (2006.01) | |

(52) U.S. Cl.
CPC .............. *C12N 9/88* (2013.01); *C12N 9/1051* (2013.01); *C12N 9/1205* (2013.01); *C12N 9/90* (2013.01); *C12P 19/02* (2013.01); *C12P 19/24* (2013.01); *C12Y 204/01025* (2013.01); *C12Y 207/01002* (2013.01); *C12Y 207/01144* (2013.01); *C12Y 401/0204* (2013.01); *C12Y 503/01009* (2013.01); *C12Y 504/02002* (2013.01)

(58) Field of Classification Search
CPC ...... C12Y 401/0204; C12Y 207/01002; C12Y 504/02002; C12Y 207/01144; C12Y 503/01009; C12Y 204/01025; C12P 19/24; C12P 19/02; C12N 9/1051; C12N 9/88; C12N 9/90; C12N 9/1205
See application file for complete search history.

(56) References Cited

U.S. PATENT DOCUMENTS

| | | | |
|---|---|---|---|
| 10,138,506 B2* | 11/2018 | Wichelecki | .... C12Y 207/01144 |
| 10,865,395 B2* | 12/2020 | Yang | .................. C12N 9/2457 |
| 2016/0186162 A1 | 6/2016 | Oh et al. | |
| 2020/0087689 A1* | 3/2020 | Yang | .............. C12Y 207/01144 |

FOREIGN PATENT DOCUMENTS

| | | |
|---|---|---|
| CN | 106399427 A | 2/2017 |
| EP | 3604516 A1 | 2/2020 |
| KR | 10-744479 | 7/2007 |
| KR | 10-0964091 | 6/2010 |
| KR | 10-1057873 | 8/2011 |
| KR | 10-1368731 | 2/2014 |
| KR | 10-2014-0143109 A | 12/2014 |
| KR | 10-1480422 | 1/2015 |
| KR | 10-2015-0081823 A | 7/2015 |
| KR | 10-1550796 | 9/2015 |
| WO | WO 2006/058092 A2 | 6/2006 |
| WO | WO 2017/059278 A1 | 4/2017 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Cabrera et al., Ribokinase family evolution and the role of conserved residues at the active site of the PfkB subfamily representative, Pfk-2 from *Escherichia coli* Arch. Biochem. Biophys., 2010, vol. 502: 23-30. (Year: 2010).*
Devos et al., Practical limits of function prediction. Proteins: Structure, Function, and Genetics. 2000, vol. 41: 98-107. (Year: 2000).*
Fordyce AM., A Comparative Study of Phosphofructokinase and Tagatose 6-Phosphate Kinase From *Streptoctococcus lactis*. Ph.D. Thesis, 1982, pp. 1-265, Massey Univ., New Zealand. (Year: 1982).*
Miallau et al., Structures of *Staphylococcus aureus* D-Tagatose-6-phosphate Kinase Implicate Domain Motions in Specificity and Mechanism. The J. Biol. Chem., 2007, vol. 282(27): 19948-19957. (Year: 2007).*
Nho et al., Comparative Genomic Characterization of Three *Streptococcus* parauberis Strains in Fish Pathogen, as Assessed by Wide-Genome Analyses. PLOS One, 2013, vol. 8(11), pp. 1-13. (Year: 2013).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*

(Continued)

*Primary Examiner* — Ganapathirama Raghu
(74) *Attorney, Agent, or Firm* — Squire Patton Boggs (US) LLP

(57) ABSTRACT

Provided are a composition for producing tagatose, comprising fructose-6-phosphate 4-epimerase, and a method of producing tagatose using the same.

8 Claims, 7 Drawing Sheets
Specification includes a Sequence Listing.

(56) References Cited

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
Kisselev L., Polypeptide release factors in prokaryotes and eukaryotes: same function, different structure. Structure, 2002, vol. 10: 8-9. (Year: 2002).*
Sadowski et al., The sequence-structure relationship and protein function prediction. Current Opinion in Structural Biology, 2009, vol. 19: 357-362. (Year: 2009).*
Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: 20120318, pp. 1-10. (Year: 2013).*
International Search Report and Written Opinion of the International Patent Application No. PCT/KR2018/003749, dated Jul. 30, 2018 and the English translation of the International Search Report; 15 pages.
Ito, Susumu "Catalysis, Structures, and Applications of Carbohydrate Epimerases", Journal of Applied Glycoscience, 2010, vol. 57, No. 1, pp. 1-6.
NCBI, GenBank accession No. ACM23254.1, Jan. 30, 2014.
NCBI, GenBank accession No. WP_012582774.1, May 25, 2015; 1 page.
Wichelecki et al., "ATP-binding Cassette (ABC) Transport System Solute-binding Protein-guided Identification of Novel $_D$-Altritol and Galactitol Catabolic Pathways in Agrobacterium tumefaciens C58", The Journal of Biological Chemistry, Nov. 27, 2015, vol. 290, No. 48, pp. 28963-28976.
Database UniProt, "SubName: Full=Putative tagatose-6-phosphate kinase {ECO:00003131EMBL:BAJ62431.1}; EC=2.7.1.144 {ECO:00003131EMBL:BAJ62431.1};", Apr. 5, 2011, XP055752482; 1 page.
Database UniProt, "SubName: Full=Tagatose-6-phosphate kinase {ECO:00003131EMBL:ACK41689.1}; EC=2.7.1.144 {ECO:00003131EMBL:ACK41689.1};", Mar. 3, 2009, XP055752483; 2 pages.
Database UniProt, "SubName: Full=Uncharacterized protein {ECO:00003131EMBL:KPK13642.1};", Feb. 17, 2016, XP055752670; 1 page.
Wichelecki et al., "ATP-binding Cassette (ABC) Transport System Solute-binding Protein-guided Identification of Novel d-Altritol and Galactitol Catabolic Pathways in Agrobacterium tumefaciens C58", Journal of Biological Chemistry, vol. 290, No. 48, Oct. 15, 2015, pp. 28963-28976, XP055560000.
Brinkkötter et al., "Two class IID-tagatose-bispohosphate aldolases from enteric bacteria", Arch Microbiol, 2002, vol. 177, pp. 410-419, DOI 10.1007/s00203-002-0406-6.
NCBI Reference Sequence: WP_015868068.1, Oct. 8, 2019, "D-tagatose-biophosphate aldolase, class II, non-catalytic subunit [Kosmotoga olearia]", 1 page.
Notification of the First Office Action of CN Patent Application No. 201880035931.1 dated Feb. 22, 2023, and its English translation; 22 pages.
Crow et al., "Plasmid Linkage of the D-Tagatose 6-Phosphate Pathway in *Streptococcus lactis*: Effect on Lactose and Galactose Metabolism", Journal of Bacteriology, Jan. 1983, vol. 153, No. 1, pp. 76-83.
Cai Taisheng et al., Biochemistry 2nd Edition, Fourth Military Medical University Press, Aug. 2014, p. 67.
Lv Shuxia et al., China Agricultural Press, Jul. 2003, p. 128 (clean and marked).

* cited by examiner

[FIG. 1]
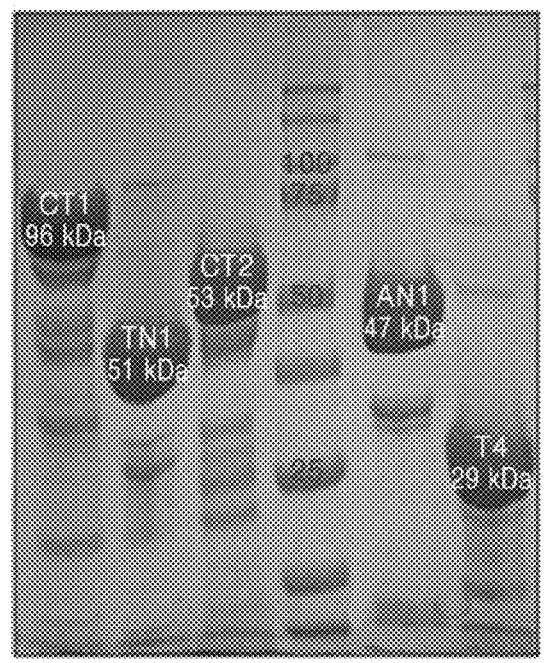
M: Protein size ladder(10~250kDa)
CT1: E. coli BL21(DE3)/pET21a-CJ_ct1
TN1: E. coli BL21(DE3)/pET21a-CJ_tn1
CT2: E. coli BL21(DE3)/pET21a-CJ_ct2
AN1: E. coli BL21(DE3)/pBT7-C-His-an1
T4: E. coli BL21(DE3)/pET21a-CJ_t4

[FIG. 2]
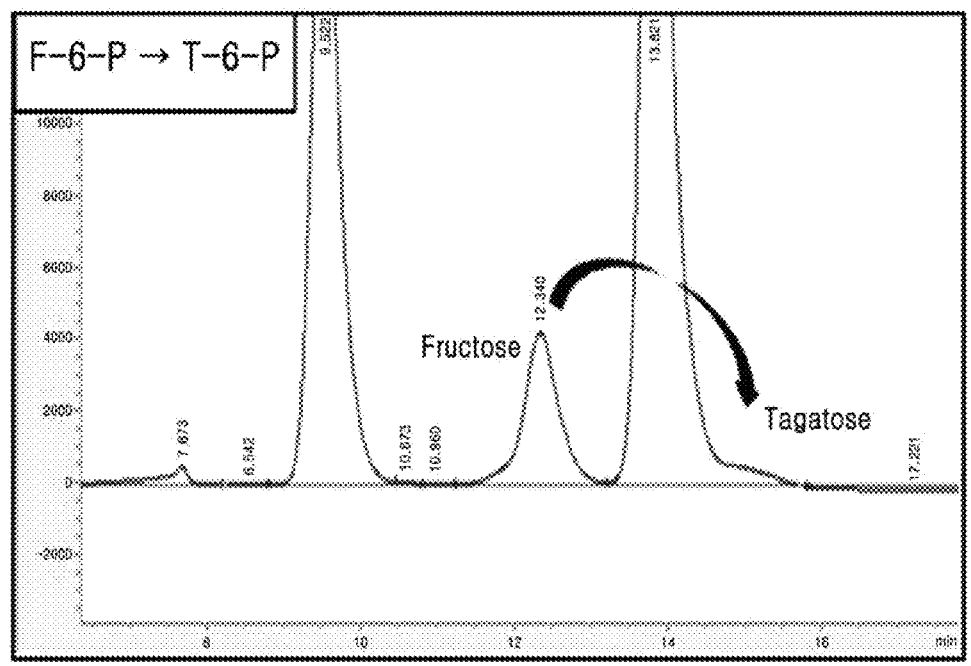

[FIG. 3]
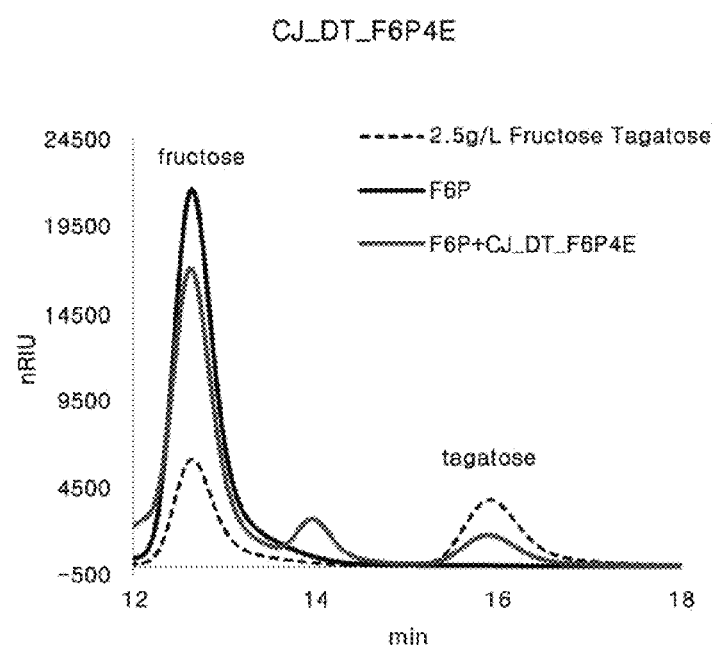

[FIG. 4]
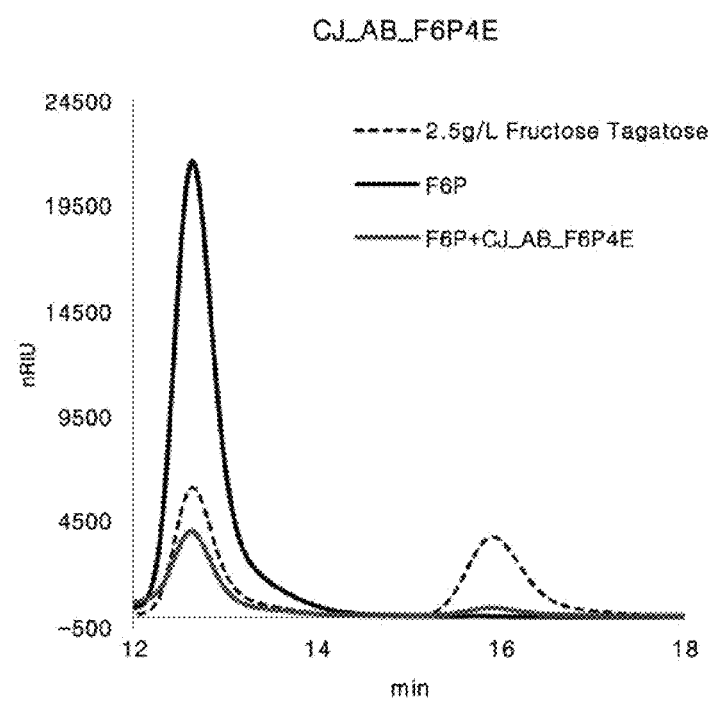

[FIG. 5]
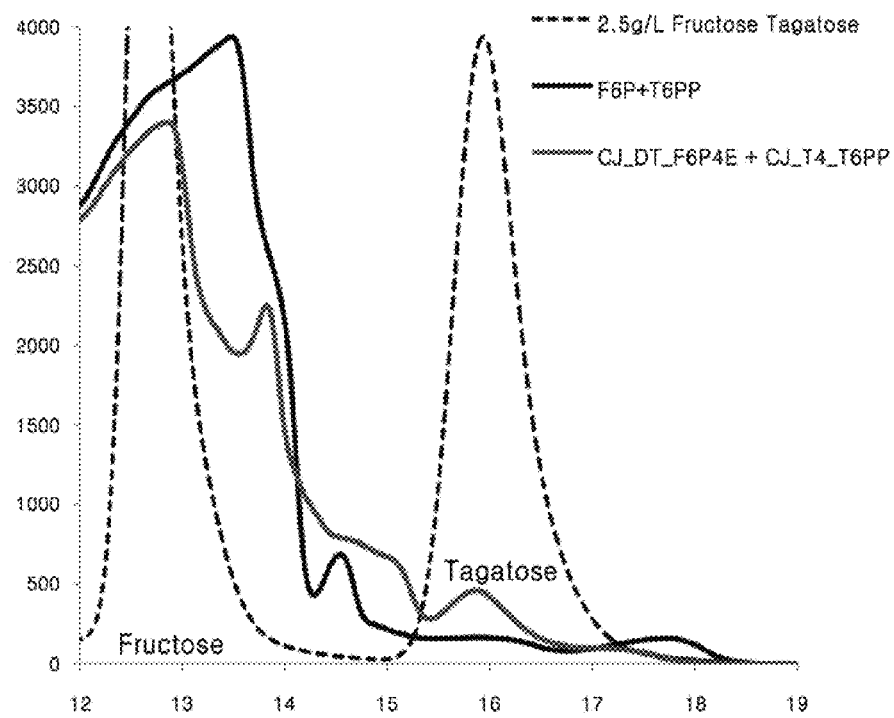

[FIG. 6]
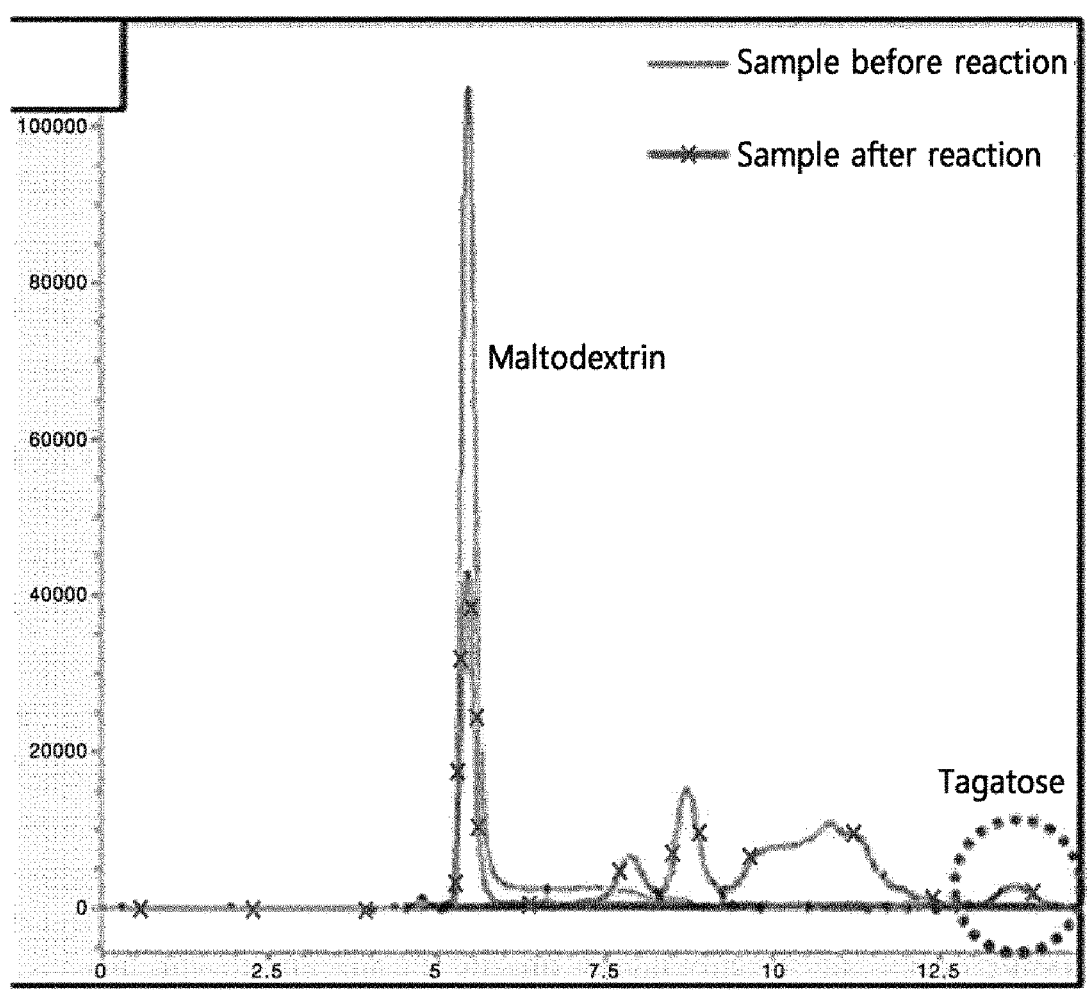

[FIG. 7]
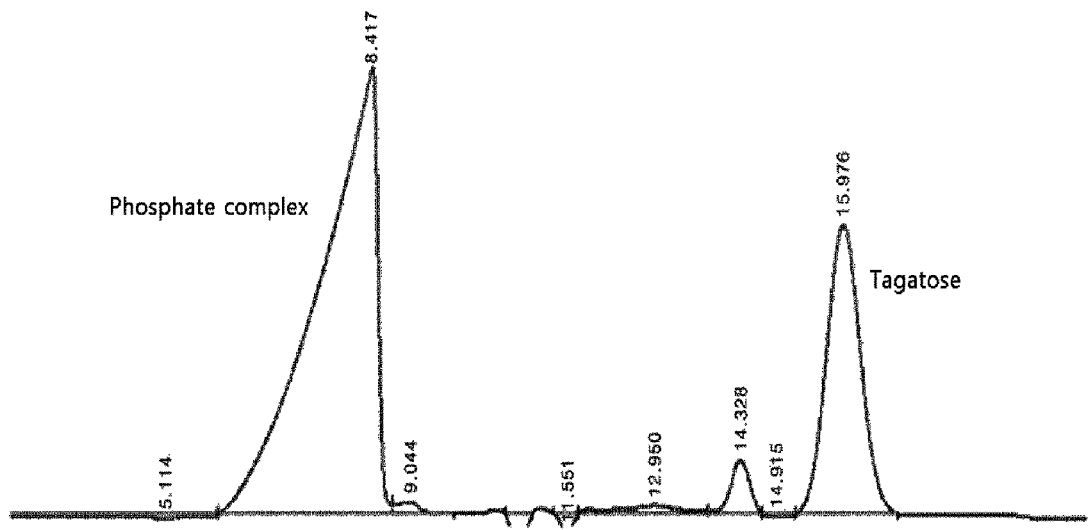

COMPOSITION FOR PRODUCING TAGATOSE AND METHOD OF PRODUCING TAGATOSE USING THE SAME

CROSS-REFERENCE TO RELATED APPLICATIONS

This application is the National Stage of International Application No. PCT/KR2018/003749, filed Mar. 30, 2018, which claims the benefit of Korean Application No. 10-2017-0042165, filed Mar. 31, 2017, the contents of which are hereby incorporated by reference in their entirety.

BACKGROUND OF THE INVENTION

1. Field of the Invention

The present disclosure relates to a composition for producing tagatose-6-phosphate, comprising fructose-6-phosphate 4-epimerase, and a method of producing tagatose using the same.

2. Description of the Related Art

Conventional methods of producing tagatose include a chemical method (a catalytic reaction) and a biological method (an isomerization enzyme reaction) of using galactose as a main raw material (see Korean Patent No. 10-0964091). However, the price of lactose which is a basic raw material of galactose used as a main raw material in the known production methods is unstable, depending on produced amounts, supply, and demand of raw milk and lactose in global markets, etc. Thus, there is a limitation in the stable supply thereof. To overcome the problem of the conventional methods of producing tagatose, methods of producing tagatose from D-fructose having a low price and steady supply using hexuronate C4-epimerase have been reported (2011. Appl Biochem Biotechnol. 163:444-451; Korean Patent No. 10-1550796). However, there is a limitation in that the isomerization has a low conversion rate.

Tagatose-bisphosphate aldolase (EC 4.1.2.40) is known to produce glycerone phosphate and D-glyceraldehyde 3-diphosphate from D-tagatose 1,6-bisphosphate as a substrate, as in the following [Reaction Scheme 1], and to participate in a galactose metabolism. However, there have been no studies regarding whether the tagatose-bisphosphate aldolase has activity to convert fructose-6-phosphate into tagatose-6-phosphate.

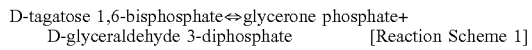

[Reaction Scheme 1]

Under this background, the present inventors have conducted extensive studies to develop an enzyme which may be used in the production of tagatose, and as a result, they found that tagatose-bisphosphate aldolase (EC 4.1.2.40) has the ability to convert glucose-6-phosphate into tagatose-6-phosphate, thereby completing the present disclosure.

Accordingly, glucose or starch may be used as a raw material to sequentially produce glucose-1-phosphate and glucose-6-phosphate, and then tagatose-bisphosphate aldolase of the present disclosure may be used to convert glucose-6-phosphate into tagatose-6-phosphate, and tagatose-6-phosphate phosphatase which performs an irreversible reaction pathway may be used to produce tagatose while remarkably increasing a conversion rate of glucose or starch into tagatose.

SUMMARY OF THE INVENTION

An object of the present disclosure is to provide a composition useful for the production of tagatose-6-phosphate, comprising tagatose-bisphosphate aldolase, a microorganism expressing the tagatose-bisphosphate aldolase, or a culture of the microorganism.

Another object of the present disclosure is to provide a composition useful for the production of tagatose, comprising tagatose-bisphosphate aldolase, a microorganism expressing the tagatose-bisphosphate aldolase, or a culture of the microorganism; and tagatose-6-phosphate phosphatase, the microorganism expressing the tagatose-6-phosphate phosphatase, or a culture of the microorganism.

Another object of the present disclosure is to provide a method of producing tagatose, comprising converting fructose-6-phosphate into tagatose-6-phosphate by contacting fructose-6-phosphate with tagatose-bisphosphate aldolase, a microorganism expressing the tagatose-bisphosphate aldolase, or a culture of the microorganism, wherein the method may further comprise converting tagatose-6-phosphate into tagatose by contacting tagatose-6-phosphate with tagatose-6-phosphate phosphatase, a microorganism expressing the tagatose-6-phosphate phosphatase, or a culture of the microorganism.

Other objects and advantages of the present disclosure will be described in more detail with reference to the following description along with the accompanying claims and drawings. Since contents that are not described in the present specification may be sufficiently recognized and inferred by those skilled in the art or similar art, a description thereof will be omitted.

BRIEF DESCRIPTION OF THE DRAWINGS

FIGS. 1A to 1D are results of HPLC chromatography showing that tagatose-bisphosphate aldolases (CJ_KO_F6P4E, CJ_RM_F6P4E, CJ_RP_F6P4E, and CJ_LP_F6P4E) of one embodiment of the present disclosure have fructose-6-phosphate-4-epimerase activity;

FIGS. 2A and 2B are results of HPLC chromatography showing that treatment of fructose-6-phosphate with tagatose-bisphosphate aldolase (CJ_KO_F6P4E and CJ_RP_F6P4E) and tagatose-6-phosphate phosphatase (CJ_T4) converts fructose-6-phosphate into tagatose in one embodiment of the present disclosure;

FIG. 3 is a result of HPLC chromatography showing that T4 which is an enzyme of one embodiment of the present disclosure has tagatose-6-phosphate phosphatase activity;

FIG. 4 is a result of protein electrophoresis (SDS-PAGE) to analyze molecular weights of enzymes used in the production pathways of tagatose from starch, sucrose, or glucose in one embodiment of the present disclosure, wherein M represents a protein size ladder (size marker, Bio-RAD, USA);

FIG. 5 is a result of HPLC chromatography showing that TD1(CJ_TD1_F6P4E) which is an enzyme of one embodiment of the present disclosure has fructose-6-phosphate-4-epimerase activity; and FIG. 6 is a result of HPLC chromatography showing that when all of the enzymes involved in the production pathway of tagatose from maltodextrin were added at the same time, tagatose was produced by complex enzyme reactions, wherein CJ_AN1_F6P4E was used as tagatose-6-phosphate kinase;

FIG. 7 is a result of HPLC chromatography showing that T4 which is an enzyme of the present disclosure has tagatose-6-phosphate phosphatase activity.

DETAILED DESCRIPTION OF THE PREFERRED EMBODIMENTS

Hereinafter, the present disclosure will be described in detail as follows. Meanwhile, each description and embodiment disclosed in this disclosure may be applied to other descriptions and embodiments to common things. Further, all combinations of various elements disclosed in this disclosure fall within the scope of the present disclosure. Further, the scope of the present disclosure is not limited by the specific description described below.

To achieve one object of the present disclosure, an aspect of the present disclosure provides a composition for producing tagatose-6-phosphate, comprising tagatose-bisphosphate aldolase, a microorganism expressing the tagatose-bisphosphate aldolase, or a culture of the microorganism.

The tagatose-bisphosphate aldolase (EC 4.1.2.40) is known to produce glycerone phosphate and D-glyceraldehyde 3-diphosphate from D-tagatose 1,6-bisphosphate as a substrate, and to participate in a galactose metabolism. For example, the tagatose-bisphosphate aldolase may be any one without limitation as long as it is able to produce tagatose-6-phosphate from fructose-6-phosphate as a substrate.

Specifically, the tagatose-bisphosphate aldolase may be a polypeptide consisting of an amino acid sequence of SEQ ID NO: 1, 3, 5, 7, or 9, or comprise a polypeptide having at least 80%, 90%, 95%, 97%, or 99% homology with the amino acid sequence of SEQ ID NO: 1, 3, 5, 7, or 9. It is also apparent that a polypeptide having the homology and an amino acid sequence exhibiting the efficacy (i.e., fructose-6-phosphate C4-epimerization activity to convert fructose-6-phosphate into tagatose-6-phosphate by epimerizing fructose-6-phosphate at C4 position of fructose) corresponding to the protein consisting of the amino acid sequence of SEQ ID NO: 1, 3, 5, 7, or 9 is also included in the scope of the present disclosure, although it has an amino acid sequence, of which a partial sequence is deleted, modified, substituted, or added. Further, a probe which may be produced from the known nucleotide sequence, for example, a polypeptide encoded by a polynucleotide which is hybridizable with a complementary sequence to all or a part of a nucleotide sequence encoding the polypeptide under stringent conditions may be also included without limitation, as long as it has the fructose-6-phosphate C4-epimerization activity. Therefore, the composition for producing tagatose-6-phosphate may further comprise fructose-6-phosphate. Further, the composition may comprise one or more of tagatose-bisphosphate aldolase consisting of the amino acid sequence of 1, 3, 5, 7, or 9.

The present disclosure revealed that the 'tagatose-bisphosphate aldolase' exhibits the fructose-6-phosphate 4-epimerization activity to convert fructose-6-phosphate into tagatose-6-phosphate by epimerizing fructose-6-phosphate at C4 position. In the present disclosure, therefore, the 'tagatose-bisphosphate aldolase' may be used interchangeably with 'fructose-6-phosphate C4 epimerase'.

As used herein, the term "stringent conditions" means conditions under which specific hybridization between polynucleotides is allowed. These conditions depend on the length of the polynucleotide and the degree of complementation, and variables are well known in the art, and specifically described in a literature (e.g., J. Sambrook et al., infra). The stringent conditions may include, for example, conditions under which genes having high homology, 80% or higher homology, 90% or higher homology, 95% or higher homology, 97% or higher homology, or 99% or higher homology, are hybridized with each other and genes having homology lower than the above homology are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS. The probe used in the hybridization may be a part of a complementary sequence of the nucleotide sequence. Such a probe may be produced by PCR using oligonucleotides produced based on the known sequence as primers and a DNA fragment containing these nucleotide sequences as a template. Further, those skilled in the art may adjust the temperature and the salt concentration of the washing solution according to factors such as the length of the probe, if necessary.

As used herein, the term "homology" refers to a percentage of identity between two polypeptide moieties. Sequence correspondence from one moiety to another may be determined by a known technique in the art. For example, the homology may be determined by directly aligning the sequence information of two polypeptide molecules, e.g., parameters such as score, identity, and similarity, etc., using a computer program that is readily available and capable of aligning sequence information (e.g., BLAST 2.0). Additionally, the homology between polynucleotides may be determined by hybridizing the polynucleotides under a condition for forming a stable double-strand in the homologous regions followed by digesting the hybridized strand by a single-strand-specific nuclease to determine the size of digested fragments.

In a specific embodiment, the fructose-6-phosphate-4-epimerase of the present disclosure may be an enzyme derived from a thermophilic microorganism or a variant thereof, for example, an enzyme derived from *Thermanaerothrix* sp. or a variant thereof, an enzyme derived from *Kosmotoga* sp. or a variant thereof, an enzyme derived from *Rhodothermus* sp. or a variant thereof, an enzyme derived from *Limnochorda* sp. or a variant thereof, and specifically, an enzyme derived from *Thermanaerothrix daxensis, Kosmotoga olearia, Rhodothermus marinus, Rhodothermus profundi*, or *Limnochorda pilosa*, but is not limited thereto.

The fructose-6-phosphate-4-epimerase of the present disclosure or a variant thereof is characterized by converting D-fructose-6-phosphate into D-tagatose-6-phosphate by epimerizing D-fructose-6-phosphate at C4 position. The fructose-6-phosphate-4-epimerase of the present disclosure may be an enzyme which is known to have tagatose-bisphosphate aldolase activity, and the tagatose-bisphosphate aldolase produces glycerone phosphate and D-glyceraldehyde 3-diphosphate from D-tagatose 1,6-bisphosphate as a substrate, and participates in a galactose metabolism. The present disclosure newly revealed that the tagatose-bisphosphate aldolase has the fructose-6-phosphate-4-epimerase activity. Accordingly, one embodiment of the present disclosure relates to novel use of the tagatose-bisphosphate aldolase including using the tagatose-bisphosphate aldolase as the fructose-6-phosphate-4-epimerase in the production of tagatose-6-phosphate from fructose-6-phosphate. Further, another embodiment of the present disclosure relates to a method of producing tagatose-6-phosphate from fructose-6-phosphate using the tagatose-bisphosphate aldolase as the fructose-6-phosphate-4-epimerase.

In one embodiment, the fructose-6-phosphate-4-epimerase of the present disclosure may be an enzyme having high heat resistance. Specifically, the fructose-6-phosphate-4-epimerase of the present disclosure may exhibit 50% to 100%, 60% to 100%, 70% to 100%, or 75% to 100% of its maximum activity at 50° C. to 70° C. More specifically, the fructose-6-phosphate-4-epimerase of the present disclosure may exhibit 80% to 100% or 85% to 100% of its maximum activity at 55° C. to 65° C., 60° C. to 70° C., 55° C., 60° C., or 70° C.

Furthermore, the fructose-6-phosphate-4-epimerase consisting of the amino acid sequence of SEQ ID NO: 1, 3, 5, 7, or 9 may be, but is not limited to, encoded by a nucleotide sequence of SEQ ID NO: 2, 4, 6, 8, or 10, respectively.

The fructose-6-phosphate-4-epimerase of the present disclosure or a variant thereof may be obtained by transforming a microorganism such as *Escherichia.coli* with DNA expressing the enzyme of the present disclosure or the variant thereof, e.g., SEQ ID NO: 2, 4, 6, 8, or 10, culturing the microorganism to obtain a culture, disrupting the culture, and then performing purification using a column, etc. The microorganism for transformation may include *Corynebacterium glutamicum, Aspergillus oryzae,* or *Bacillus subtilis,* in addition to *Escherichia.coli*. In a specific embodiment, the transformed microorganism may be *Escherichia.coli* BL21(DE3)/CJ_KO_F6P4E, *Escherichia.coli* BL21(DE3)/CJ_RM_F6P4E, *Escherichia.coli* BL21(DE3)/CJ_RP_F6P4E, *Escherichia.coli* BL21(DE3)/CJ_LP_F6P4E, or *Escherichia.coli* BL21(DE3)/pBT7-C-His-CJt_d1. These microorganisms were deposited at the Korean Culture Center of Microorganisms which is an International Depositary Authority under the provisions of the Budapest Treaty with Accession No. KCCM11999P (*Escherichia.coli* BL21(DE3)/CJ_KO_F6P4E) (date of deposit: Mar. 24, 2017), KCCM12096P (*Escherichia.coli* BL21(DE3)/CJ_RM_F6P4E) (date of deposit: Aug. 11, 2017), KCCM12097P (*Escherichia.coli* BL21(DE3)/CJ_RP_F6P4E) (date of deposit: Aug. 11, 2017), KCCM12095P (*Escherichia.coli* BL21(DE3)/CJ_LP_F6P4E) (date of deposit: Aug. 11, 2017), and KCCM11995P (*Escherichia.coli* BL21(DE3)/pBT7-C-His-CJ_td1) (date of deposit: Mar. 20, 2017), respectively.

The fructose-6-phosphate-4-epimerase used in the present disclosure may be provided by using a nucleic acid encoding the same.

As used herein, the term "nucleic acid" means that it encompasses DNA or RNA molecules, wherein nucleotides which are basic constituent units in the nucleic acid may include not only natural nucleotides but also analogues with modification of sugar or base (see: Scheit, Nucleotide Analogs, John Wiley, New York (1980); Uhlman and Peyman, Chemical Reviews, 90:543-584(1990)).

The nucleic acid of the present disclosure may be a nucleic acid encoding the polypeptide consisting of the amino acid sequence of SEQ ID NO: 1, 3, 5, 7, or 9 of the present disclosure or a nucleic acid encoding a polypeptide having at least 80%, 90%, 95%, 97% or 99% homology with the fructose-6-phosphate-4-epimerase of the present disclosure and having the fructose-6-phosphate-4-epimerase activity. For example, the nucleic acid encoding the fructose-6-phosphate-4-epimerase consisting of the amino acid sequence of SEQ ID NO: 1 may be a nucleic acid having at least 80%, 90%, 95%, 97%, 99% or 100% homology with the nucleotide sequence of SEQ ID NO: 2. Further, the nucleic acid encoding the fructose-6-phosphate-4-epimerase consisting of the amino acid sequence of SEQ ID NO: 3, 5, 7, or 9 may be a nucleic acid having at least 80%, 90%, 95%, 97%, 99% or 100% homology with the nucleotide sequence of SEQ ID NO: 4, 6, 8, or 10 corresponding thereto, respectively. It is also apparent that the nucleic acid of the present disclosure may include a nucleic acid which is translated into the fructose-6-phosphate-4-epimerase of the present disclosure due to codon degeneracy or a nucleic acid which hybridizes with a nucleic acid consisting of a nucleotide sequence complementary to the nucleotide sequence of SEQ ID NO: 2, 4, 6, 8, or 10 under stringent conditions and encodes the polypeptide having the fructose-6-phosphate-4-epimerase activity of the present disclosure.

The microorganism expressing the fructose-6-phosphate-4-epimerase which may be used in the present disclosure may be a microorganism comprising a recombinant vector comprising the nucleic acid.

The vector may be operably linked to the nucleic acid of the present disclosure. As used herein, the term "operably linked" means that a nucleotide expression regulatory sequence and a nucleotide sequence encoding a targeted protein are operably linked to each other to perform the general functions, thereby affecting expression of the encoding nucleotide sequence. The operable linkage to the vector may be produced using a genetic recombination technology known in the art, and the site-specific DNA cleavage and linkage may be produced using restriction enzymes and ligases known in the art.

As used herein, the term "vector" refers to any mediator for cloning and/or transferring of bases into an organism, such as a host cell. The vector may be a replicon that is able to bring the replication of combined fragments in which different DNA fragments are combined. Herein, the term "replicon" refers to any genetic unit (e.g., plasmid, phage, cosmid, chromosome, virus) which functions as a self-unit of DNA replication in vivo, i.e., which is able to be replicated by self-regulation. As used herein, the term "vector" may comprise viral and non-viral mediators for introducing the bases into the organism, e.g., a host cell, in vitro, ex vivo, or in vivo, and may also comprise a minicircular DNA, a transposon such as Sleeping Beauty (Izsvak et al. J. Mol. Biol. 302:93-102 (2000)), or an artificial chromosome. Examples of the vector commonly used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc., may be used; and as a plasmid vector, those based on pBR, pUC, pBluescriptII, pGEM, pTZ, pCL, and pET, etc., may be used. The vectors that may be used in the present disclosure are not particularly limited, but any known expression vector may be used. Further, the vector may be a recombinant vector characterized by further comprising various antibiotic resistance genes. As used herein, the term "antibiotic resistance gene" refers to a gene having resistance against an antibiotic, and a cell having this gene survives in an environment treated with the corresponding antibiotic. Therefore, the antibiotic resistance gene is used as a selectable marker during production of a large amount of plasmids in *Escherichia.coli*. The antibiotic resistance gene in the present disclosure is not a factor that greatly influences expression efficiency according to optimal combinations of vectors which is a key technology of the present disclosure, and thus an antibiotic resistance gene that is generally used as a selectable marker may be used without limitation. Specific examples may include a resistance gene against ampicilin, tetracyclin, kanamycin, chloroamphenicol, streptomycin, or neomycin, etc.

The microorganism expressing the fructose-6-phosphate-4-epimerase which may be used in the present disclosure may be obtained by a method of introducing the vector comprising the nucleic acid encoding the enzyme into a host cell, and a method of transforming the vector may be any method as long as it is able to introduce the nucleic acid into the cell. An appropriate standard technique known in the art may be selected and performed. Electroporation, calcium phosphate co-precipitation, retroviral infection, microinjection, a DEAE-dextran method, a cationic liposome method, and a heat shock method may be included, but is not limited thereto.

As long as the transformed gene may be expressed in the host cell, it may be inserted into the chromosome of the host cell, or it may exist extrachromosomally. Further, the gene comprises DNA and RNA as a polynucleotide encoding a polypeptide, and any form may be used without limitation, as long as it may be introduced into the host cell and expressed therein. For example, the gene may be introduced into the host cell in the form of an expression cassette, which is a polynucleotide construct comprising all elements required for its autonomous expression. Commonly, the expression cassette may comprise a promoter operably linked to the gene, transcriptional termination signals, ribosome binding sites, and translation termination signals. The expression cassette may be in the form of a self-replicable expression vector. In addition, the gene as it is or in the form of a polynucleotide construct may be introduced into the host cell and operably linked to sequences required for expression in the host cell.

The microorganism of the present disclosure may include either a prokaryotic microorganism or a eukaryotic microorganism, as long as it is a microorganism capable of producing the fructose-6-phosphate-4-epimerase of the present disclosure by comprising the nucleic acid of the present disclosure or the recombinant vector of the present disclosure. For example, the microorganism may include microorganism strains belonging to the genus *Escherichia*, the genus *Erwinia*, the genus *Serratia*, the genus *Providencia*, the genus *Corynebacterium*, and the genus *Brevibacterium*, and specifically, it may be *Escherichia.coli* or *Corynebacterium glutamicum*, but is not limited thereto. Specific examples of the microorganism may include *Escherichia.coli* BL21(DE3)/CJ_KO_F6P4E, *Escherichia.coli* BL21(DE3)/CJ_RM_F6P4E, *Escherichia.coli* BL21(DE3)/CJ_RP_F6P4E, *Escherichia.coli* BL21(DE3)/CJ_LP_F6P4E, *Escherichia.coli* BL21(DE3)/pBT7-C-His-CJ_td1, etc.

The microorganism of the present disclosure may include any microorganism capable of expressing the fructose-6-phosphate-4-epimerase of the present disclosure or related enzymes according to various known methods, in addition to introduction of the nucleic acid or the vector.

The culture of the microorganism of the present disclosure may be produced by culturing, in a medium, the microorganism capable of expressing the tagatose-bisphosphate aldolase of the present disclosure or related enzymes.

As used herein, the term "culturing" means that the microorganism is allowed to grow under appropriately controlled environmental conditions. The culturing process of the present disclosure may be carried out according to an appropriate medium and culture conditions known in the art. The culturing process may be easily adjusted by those skilled in the art according to the strain to be selected. The step of culturing the microorganism may be, but is not particularly limited to, carried out by a batch process, a continuous process, or a fed batch process etc. With regard to the culture conditions, a proper pH (e.g., pH 5 to 9, specifically pH 7 to 9) may be adjusted using a basic compound (e.g., sodium hydroxide, potassium hydroxide, or ammonia) or an acidic compound (e.g., phosphoric acid or sulfuric acid), but is not particularly limited thereto. Additionally, an antifoaming agent such as fatty acid polyglycol ester may be added during the culturing process to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture. The culture temperature may be maintained from 25° C. to 40° C., and specifically, from 30° C. to 37° C., but is not limited thereto. The culturing may be continued until the desired amount of useful materials is obtained, and specifically for about 0.5 hours to about 60 hours, but is not limited thereto. Furthermore, the culture medium to be used may comprise, as carbon sources, sugars and carbohydrates (e.g., glucose, sucrose, lactose, fructose, maltose, molasses, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), and organic acids (e.g., acetic acid) etc. These substances may be used individually or in a mixture, but are not limited thereto. Nitrogen sources may include nitrogen-containing organic compounds (e.g., peptone, yeast extract, meat extract, malt extract, corn steep liquor, soybean meal, and urea) or inorganic compounds (e.g., ammonium sulfate, ammonium chloride, ammonium phosphate, ammonium carbonate, and ammonium nitrate) etc. These nitrogen sources may also be used individually or in a mixture, but are not limited thereto. Phosphorus sources may include potassium dihydrogen phosphate, dipotassium hydrogen phosphate, or the corresponding sodium-containing salts etc. These nitrogen sources may also be used individually or in a mixture, but are not limited thereto. The culture medium may comprise essential growth stimulators, such as metal salts (e.g., magnesium sulfate or iron sulfate), amino acids, and vitamins.

Another aspect of the present disclosure provides a composition for producing tagatose, comprising tagatose-bisphosphate aldolase, a microorganism expressing the tagatose-bisphosphate aldolase, or a culture of the microorganism; and tagatose-6-phosphate phosphatase, the microorganism expressing the tagatose-6-phosphate phosphatase, or a culture of the microorganism.

The description of the composition for producing tagatose-6-phosphate may be also applied to the composition for producing tagatose. The tagatose-6-phosphate phosphatase of the present disclosure may be any protein without limitation, as long as it has activity to convert tagatose-6-phosphate into tagatose by eliminating a phosphate group of the tagatose-6-phosphate. The tagatose-6-phosphate phosphatase of the present disclosure may be an enzyme derived from a heat-resistant microorganism, for example, an enzyme derived from *Thermotoga* sp. or a variant thereof, specifically, an enzyme derived from *Thermotoga maritima* or a variant thereof.

According to one embodiment of the present disclosure, the tagatose-6-phosphate phosphatase of the present disclosure may be a protein which consists of an amino acid sequence of SEQ ID NO: 11, a sequence having a genetic homology of 70%, 75%, 80%, 85%, 90%, 95%, 97%, 99%, or 100% thereto, or a genetic homology within the range determined by any two values of the above values. According to one embodiment of the present disclosure, the tagatose-6-phosphate phosphatase consisting of the amino acid sequence of SEQ ID NO: 11 of the present disclosure may be encoded by a nucleotide sequence of SEQ ID NO: 12.

The composition for producing tagatose of the present disclosure may further comprise glucose-6-phosphate isomerase, a microorganism expressing the glucose-6-phosphate isomerase, or a culture of the microorganism. In the presence of the enzyme, glucose-6-phosphate may be isomerized to produce fructose-6-phosphate. The glucose-6-phosphate-isomerase of the present disclosure may include any protein without limitation, as long as it has activity to isomerize glucose-6-phosphate into fructose-6-phosphate. The glucose-6-phosphate-isomerase of the present disclosure may be an enzyme derived from a heat-resistant microorganism, for example, an enzyme derived from *Thermotoga* sp. or a variant thereof, specifically, an enzyme derived from *Thermotoga maritima* or a variant thereof. According to one embodiment of the present disclosure, the glucose-6-phosphate-isomerase of the present disclosure may be a protein which consists of an amino acid sequence of SEQ ID NO: 13, a sequence having a genetic homology of 70%, 75%, 80%, 85%, 90%, 95%, 97%, 99%, or 100% thereto, or a homology within the range determined by any two values of the above values. According to one embodiment of the present disclosure, the glucose-6-phosphate-isomerase consisting of the amino acid sequence of SEQ ID NO: 13 of the present disclosure may be encoded by a nucleotide sequence of SEQ ID NO: 14.

The composition for producing tagatose of the present disclosure may further comprise phosphoglucomutase, a microorganism expressing the phosphoglucomutase, or a culture of the microorganism. The enzyme catalyzes a reversible reaction of converting glucose-1-phosphate into glucose-6-phosphate or converting glucose-6-phosphate into glucose-1-phosphate. The phosphoglucomutase of the present disclosure may include any protein without limitation, as long as it has activity to convert glucose-1-phosphate into glucose-6-phosphate or to convert glucose-6-phosphate into glucose-1-phosphate. The phosphoglucomutase of the present disclosure may be an enzyme derived from a heat-resistant microorganism, for example, an enzyme derived from *Thermotoga* sp. or a variant thereof, specifically, an enzyme derived from *Thermotoga neapolitana* or a variant thereof. According to one embodiment of the present disclosure, the phosphoglucomutase of the present disclosure may be a protein which consists of an amino acid sequence of SEQ ID NO: 15, a sequence having a genetic homology of 70%, 75%, 80%, 85%, 90%, 95%, 97%, 99%, or 100% thereto, or within the range determined by any two values of the above values. According to one embodiment of the present disclosure, the phosphoglucomutase consisting of the amino acid sequence of SEQ ID NO: 15 of the present disclosure may be encoded by a nucleotide sequence of SEQ ID NO: 16.

The composition for producing tagatose of the present disclosure may further comprise glucokinase, a microorganism expressing the glucokinase, or a culture of the microorganism. The glucokinase of the present disclosure may include any protein without limitation, as long as it has activity to phosphorylate glucose. The glucokinase of the present disclosure may be an enzyme derived from a heat-resistant microorganism, for example, an enzyme derived from *Deinococcus* sp. or *Anaerolinea* sp., or a variant thereof, specifically, an enzyme derived from *Deinococcus geothermalis* or *Anaerolinea thermophila*, or a variant thereof. The glucokinase of the present disclosure may include any protein without limitation, as long as it has activity to convert glucose into glucose-6-phosphate. Specifically, the glucokinase of the present disclosure may be a phosphate-dependent glucokinase. According to one embodiment of the present disclosure, the glucokinase of the present disclosure may be a protein which consists of an amino acid sequence of SEQ ID NO: 17 or 19, a sequence having a genetic homology of 70%, 75%, 80%, 85%, 90%, 95%, 97%, 99%, or 100% thereto, or a genetic homology within the range determined by any two values of the above values. According to one embodiment of the present disclosure, the glucokinase consisting of the amino acid sequence of SEQ ID NO: 17 of the present disclosure may be encoded by a nucleotide sequence of SEQ ID NO: 18, and the glucokinase consisting of the amino acid sequence of SEQ ID NO: 19 of the present disclosure may be encoded by a nucleotide sequence of SEQ ID NO: 20.

The composition for producing tagatose of the present disclosure may further comprise α-glucan phosphorylase, starch phosphorylase, maltodextrin phosphorylase, or sucrose phosphorylase, a microorganism expressing the same, or a culture of the microorganism. The phosphorylase may include any protein without limitation, as long as it has activity to convert starch, maltodextrin, or sucrose into glucose-1-phosphate. The phosphorylase may be an enzyme derived from a heat-resistant microorganism, for example, an enzyme derived from *Thermotoga* sp. or a variant thereof, specifically, an enzyme derived from *Thermotoga neapolitana* or a variant thereof. The phosphorylase of the present disclosure may be a protein which consists of an amino acid sequence of SEQ ID NO: 21, a sequence having a genetic homology of 70%, 75%, 80%, 85%, 90%, 95%, 97%, 99%, or 100% thereto, or a genetic homology within the range determined by any two values of the above values. According to one embodiment of the present disclosure, the phosphorylase consisting of the amino acid sequence of SEQ ID NO: 21 of the present disclosure may be encoded by a nucleotide sequence of SEQ ID NO: 22.

The composition for producing tagatose of the present disclosure may further comprise α-amylase, pullulanase, glucoamylase, sucrase, or isoamylase; a microorganism expressing the amylase, pullulanase, glucoamylase, sucrase, or isoamylase; or a culture of the microorganism expressing the amylase, pullulanase, glucoamylase, sucrase, or isoamylase.

The composition for producing tagatose of the present disclosure may comprise two or more enzymes of the above-described enzymes which may be used in the production of tagatose or transformants thereof individually, or a transformant transformed with nucleotides encoding the two or more enzymes.

The composition for producing tagatose of the present disclosure may further comprise 4-α-glucanotransferase, a microorganism expressing the 4-α-glucanotransferase, or a culture of the microorganism expressing the 4-α-glucanotransferase. The 4-α-glucanotransferase of the present disclosure may include any protein without limitation, as long as it has activity to convert glucose into starch, maltodextrin, or sucrose. The 4-α-glucanotransferase of the present disclosure may be an enzyme derived from a heat-resistant microorganism, for example, an enzyme derived from *Thermotoga* sp. or a variant thereof, specifically, an enzyme derived from *Thermotoga* maritime or a variant thereof. According to one embodiment of the present disclosure, the 4-α-glucanotransferase of the present disclosure may be a protein which consists of an amino acid sequence of SEQ ID NO: 23, a sequence having a genetic homology of 70%, 75%, 80%, 85%, 90%, 95%, 97%, 99%, or 100% thereto, or a genetic homology within the range determined by any two values of the above values. According to one embodiment of the present disclosure, the 4-α-glucanotransferase consisting of the amino acid sequence of SEQ ID NO: 23 of the present disclosure may be encoded by a nucleotide sequence of SEQ ID NO: 24.

Examples of the microorganisms which may be used in the above-described embodiments may include

*Escherichia.coli* BL21(DE3)/pET21a-CJ_ct1, *Escherichia.coli* BL21(DE3)/pET21a-CJ_ct2, *Escherichia.coli* BL21(DE3)/pET21a-CJ_tn1, *Escherichia.coli* BL21(DE3)/pET21a-CJ_tn2, and *Escherichia.coli* BL21(DE3)/pET21a-CJ_t4, etc. The recombinant microorganisms were deposited at Korean Culture Center of Microorganisms on Mar. 20, 2017 with Accession Nos. KCCM11990P (*Escherichia.coli* BL21(DE3)/pET21a-CJ_ct1), KCCM11991P (*Escherichia.coli* BL21(DE3)/pET21a-CJ_ct2), KCCM11992P (*Escherichia.coli* BL21(DE3)/pET21a-CJ_tn1), KCCM11993P (*Escherichia.coli* BL21(DE3)/pET21a-CJ_tn2), KCCM11994P (*Escherichia.coli* BL21(DE3)/pET21a-CJ_t4), respectively.

The composition for producing tagatose of the present disclosure may further comprise a substance, a component, or a composition corresponding to a substrate of each of the above-described enzymes.

The composition for producing tagatose of the present disclosure may further comprise any suitable excipient commonly used in the corresponding composition for producing tagatose. The excipient may include, for example, a preservative, a wetting agent, a dispersing agent, a suspending agent, a buffer, a stabilizing agent, or an isotonic agent, etc., but is not limited thereto.

The composition for producing tagatose of the present disclosure may further comprise a metal. In one embodiment, the metal of the present disclosure may be a metal containing a divalent cation. Specifically, the metal of the present disclosure may be nickel, cobalt, aluminum, magnesium (Mg), or manganese (Mn). More specifically, the metal of the present disclosure may be a metal ion or a metal salt, and much more specifically, the metal salt may be $NiSO_4$, $MgSO_4$, $MgCl_2$, $NiCl_2$, $CoCl_2$, $CoSO_4$, $MnCl_2$, or $MnSO_4$.

Another aspect of the present disclosure relates to a method of producing tagatose-6-phosphate, comprising converting fructose-6-phosphate into tagatose-6-phosphate by contacting fructose-6-phosphate with tagatose-bisphosphate aldolase, the microorganism expressing the tagatose-bisphosphate aldolase, or the culture of the microorganism.

The description of the composition for producing tagatose-6-phosphate may be also applied to the composition for producing tagatose.

Another aspect of the present disclosure relates to a method of producing tagatose, comprising converting fructose-6-phosphate into tagatose-6-phosphate by contacting fructose-6-phosphate with tagatose-bisphosphate aldolase, the microorganism expressing the tagatose-bisphosphate aldolase, or the culture of the microorganism. The method of producing tagatose may further comprise converting tagatose-6-phosphate into tagatose by contacting tagatose-6-phosphate with tagatose-6-phosphate phosphatase, the microorganism expressing the tagatose-6-phosphate phosphatase, or the culture of the microorganism.

The method of the present disclosure may further comprise converting glucose-6-phosphate into fructose-6-phosphate by contacting glucose-6-phosphate with the glucose-6-phosphate-isomerase of the present disclosure, the microorganism expressing the glucose-6-phosphate-isomerase, or the culture of the microorganism expressing the glucose-6-phosphate-isomerase.

The method of the present disclosure may further comprise converting glucose-1-phosphate into glucose-6-phosphate by contacting glucose-1-phosphate with the phosphoglucomutase of the present disclosure, the microorganism expressing the phosphoglucomutase, or the culture of the microorganism expressing the phosphoglucomutase.

The method of the present disclosure may further comprise converting glucose into glucose-6-phosphate by contacting glucose with the glucokinase of the present disclosure, the microorganism expressing the glucokinase, or the culture of the microorganism expressing the glucokinase.

The method of the present disclosure may further comprise converting starch, maltodextrin, or sucrose into glucose-1-phosphate by contacting starch, maltodextrin, sucrose, or a combination thereof with the α-glucan phosphorylase, starch phosphorylase, maltodextrin phosphorylase, or sucrose phosphorylase of the present disclosure, the microorganism expressing the phosphorylase, or the culture of the microorganism expressing the phosphorylase.

The method of the present disclosure may further comprise converting starch, maltodextrin, or sucrose into glucose by contacting starch, maltodextrin, sucrose, or a combination thereof with the α-amylase, pullulanase, glucoamylase, sucrase, or isoamylase; the microorganism expressing the α-amylase, pullulanase, glucoamylase, sucrase, or isoamylase; or the culture of the microorganism expressing the α-amylase, pullulanase, glucoamylase, sucrase, or isoamylase.

The method of the present disclosure may further comprise converting glucose into starch, maltodextrin, or sucrose by contacting glucose with the 4-α-glucanotransferase of the present disclosure, the microorganism expressing the 4-α-glucanotransferase, or the culture of the microorganism expressing the 4-α-glucanotransferase.

Each contacting in the method of the present disclosure may be performed under conditions of pH 5.0 to pH 9.0, 30° C. to 80° C., and/or for 0.5 hours to 48 hours. Specifically, the contacting of the present disclosure may be performed under a condition of pH 6.0 to pH 9.0 or pH 7.0 to pH 9.0. Further, the contacting of the present disclosure may be performed under a temperature condition of 35° C. to 80° C., 40° C. to 80° C., 45° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50° C. to 65° C., 55° C. to 65° C., 30° C. to 60° C., 35° C. to 60° C., 40° C. to 60° C., 45° C. to 60° C., 50° C. to 60° C. or 55° C. to 60° C. Furthermore, the contacting of the present disclosure may be performed for 0.5 hours to 36 hours, 0.5 hours to 24 hours, 0.5 hours to 12 hours, 0.5 hours to 6 hours, 1 hour to 36 hours, 1 hour to 24 hours, 1 hour to 12 hours, 1 hour to 6 hours, 3 hours to 36 hours, 3 hours to 24 hours, 3 hours to 12 hours, 3 hours to 6 hours, 12 hours to 36 hours, or 18 hours to 30 hours.

In one embodiment, the contacting of the present disclosure may be performed in the presence of a metal, a metal ion, or a metal salt.

Another aspect of the present disclosure relates to a method of producing tagatose, comprising contacting the composition for producing tagatose described herein with starch, maltodextrin, sucrose, or a combination thereof; and phosphate.

In a specific embodiment of the present disclosure, a method of producing tagatose is provided, comprising:
converting glucose into glucose-6-phosphate by contacting glucose with the glucokinase of the present disclosure, the microorganism expressing the glucokinase, or the culture of the microorganism,
converting glucose-6-phosphate into fructose-6-phosphate by contacting glucose-6-phosphate with the glucose-6-phosphate-isomerase of the present disclosure, the microorganism expressing the glucose-6-phosphate-isomerase, or the culture of the microorganism, converting fructose-6-phosphate into tagatose-6-phosphate by contacting fructose-6-phosphate with the fructose-6-phosphate-4-epimerase of the present disclosure, the microorganism expressing the fructose-6-phosphate-4-epimerase, or the culture of the microorganism, and converting tagatose-6-phosphate into tagatose by contacting tagatose-6-phosphate with the tagatose-6-phosphate phosphatase of the present disclosure, the microorganism expressing the tagatose-6-phosphate phosphatase, or the culture of the microorganism.

The conversion reactions may be performed sequentially or in situ in the same reaction system. In the method, phosphate released from tagatose-6-phosphate by phosphatase may be used as a substrate of the glucokinase to produce glucose-6-phosphate. Therefore, phosphate is not accumulated, and as a result, a high conversion rate may be obtained.

In the method, glucose may be, for example, produced by converting starch, maltodextrin, or sucrose into glucose by contacting starch, maltodextrin, sucrose, or a combination thereof with α-glucan phosphorylase, starch phosphorylase, maltodextrin phosphorylase, sucrose phosphorylase of the present disclosure, the microorganism expressing the phosphorylase, or the culture of the microorganism expressing the phosphorylase. Therefore, the method according to a specific embodiment may further comprise converting starch, maltodextrin, or sucrose into glucose.

In another specific embodiment of the present disclosure, a method of producing tagatose is provided, comprising:

converting glucose-1-phosphate into glucose-6-phosphate by contacting glucose-1-phosphate with the phosphoglucomutase of the present disclosure, the microorganism expressing the phosphoglucomutase, or the culture of the microorganism, converting glucose-6-phosphate into fructose-6-phosphate by contacting glucose-6-phosphate with the glucose-6-phosphate-isomerase of the present disclosure, the microorganism expressing the glucose-6-phosphate-isomerase, or the culture of the microorganism, converting fructose-6-phosphate into tagatose-6-phosphate by contacting fructose-6-phosphate with the fructose-6-phosphate-4-epimerase of the present disclosure, the microorganism expressing the fructose-6-phosphate-4-epimerase, or the culture of the microorganism, and converting tagatose-6-phosphate into tagatose by contacting tagatose-6-phosphate with the tagatose-6-phosphate phosphatase of the present disclosure, the microorganism expressing the tagatose-6-phosphate phosphatase, or the culture of the microorganism.

The conversion reactions may be performed sequentially or in situ in the same reaction system.

In the method, glucose-1-phosphate may be, for example, produced by converting starch, maltodextrin, or sucrose into glucose-1-phosphate by contacting starch, maltodextrin, sucrose, or a combination thereof with α-glucan phosphorylase, starch phosphorylase, maltodextrin phosphorylase, sucrose phosphorylase of the present disclosure, the microorganism expressing the phosphorylase, or the culture of the microorganism expressing the phosphorylase. Therefore, the method according to a specific embodiment may further comprise converting starch, maltodextrin, or sucrose into glucose-1-phosphate. In this regard, phosphate released from tagatose-6-phosphate by phosphatase may be used as a substrate of the phosphorylase to produce glucose-1-phosphate. Therefore, phosphate is not accumulated, and as a result, a high conversion rate may be obtained.

The method may further comprise purifying the produced tagatose. The purification in the method is not particularly limited, and a method commonly used in the art to which the present disclosure pertains may be used. Non-limiting examples may include chromatography, fractional crystallization, and ion purification, etc. The purification method may be performed only by a single method or by two or more methods. For example, the tagatose product may be purified through chromatography, and separation of the sugar by the chromatography may be performed by utilizing a difference in a weak binding force between the sugar to be separated and a metal ion attached to an ion resin.

In addition, the present disclosure may further comprise performing decolorization, desalination, or both of decolorization and desalination before or after the purification step of the present disclosure. By performing the decolorization and/or desalination, it is possible to obtain a more purified tagatose product without impurities.

Hereinafter, the present disclosure will be described in more detail with reference to Examples. However, these Examples are provided for better understanding, and the disclosure is not intended to be limited by these Examples.

Example 1: Production of Recombinant Expression Vector and Transformant of Each Enzyme To provide α-glucan phosphorylase, phosphoglucomutase, glucose-6-phosphate-isomerase, 4-α-glucanotransferase which are heat-resistant enzymes needed in the production pathway of tagatose of the present disclosure, nucleotide sequences expected as the enzymes [the above enzymes are represented by SEQ ID NO: 22(CT1), SEQ ID NO: 16(CT2), SEQ ID NO: 14(TN1), and SEQ ID NO: 24(TN2), respectively] were selected from a nucleotide sequence of a thermophilic microorganism, *Thermotoga neapolitana* or *Thermotoga maritima*, which is registered in Genbank.

Based on the selected nucleotide sequences, forward primers (SEQ ID NO: 21: CT1-Fp, SEQ ID NO: 27: CT2-Fp, SEQ ID NO: 29: TN1-Fp, SEQ ID NO: 31: TN2-Fp) and reverse primers (SEQ ID NO: 26: CT1-Rp, SEQ ID NO: 28: CT2-Rp, SEQ ID NO: 30: TN1-Rp, SEQ ID NO: 32: TN2-Rp) were designed and synthesized, and the gene of each enzyme was amplified by PCR using the above primers and a genomic DNA of the *Thermotoga neapolitana* as a template. Each amplified gene of the enzymes was inserted into pET21a (Novagen) which is a plasmid vector for expression in *Escherichia.coli* using restriction enzymes, NdeI and XhoI or SalI, thereby producing recombinant expression vectors designated as pET21a-CJ_ct1, pET21a-CJ_ct2, pET21a-CJ_tn1, pET21a-CJ_tn2, respectively.

Each of the expression vectors was transformed into *Escherichia.coli* BL21(DE3) according to a common transformation method [see Sambrook et al. 1989], thereby producing transformants (transformed microorganisms) designated as *Escherichia.coli* BL21(DE3)/pET21a-CJ_ct1, *Escherichia.coli* BL21(DE3)/pET21a-CJ_ct2, *Escherichia.coli* BL21(DE3)/pET21a-CJ_tn1, *Escherichia.coli* BL21(DE3)/pET21a-CJ_tn2, respectively. These transformants were deposited at the Korean Culture Center of Microorganisms under the provisions of the Budapest Treaty on Mar. 20, 2017 with Accession Nos. KCCM11990P (*Escherichia.coli* BL21(DE3)/pET21a-

CJ_ct1), KCCM11991P (*Escherichia.coli* BL21(DE3)/ pET21a-CJ_ct2), KCCM11992P (*Escherichia.coli* BL21 (DE3)/pET21a-CJ_tn1), and KCCM11993P (*Escherichia.coli* BL21(DE3)/pET21a-CJ_tn2), respectively.

Example 2: Production of Recombinant Enzymes

*Escherichia.coli* BL21(DE3)/pET21a-CJ_ct1, *Escherichia.coli* BL21(DE3)/pET21a-CJ_ct2, *Escherichia.coli* BL21(DE3)/pET21a-CJ_tn1, *Escherichia.coli* BL21(DE3)/ pET21a-CJ_tn2 expressing each of the enzymes produced in Example 1 were seeded in a culture tube containing 5 ml of LB liquid medium, and then seed culture was performed in a shaking incubator at 37° C. until absorbance at 600 nm reached 2.0.

Each of the cultures obtained by the seed culture was seeded in a culture flask containing an LB liquid medium, and then main culture was performed. When absorbance at 600 nm reached 2.0, 1 mM IPTG was added to induce expression and production of the recombinant enzymes. During the culture, a shaking speed was maintained at 180 rpm and a culture temperature was maintained at 37° C. Each culture was centrifuged at 8,000×g and 4° C. for 20 minutes to recover cells. The recovered cells were washed with 50 mM Tris-HCl (pH 8.0) buffer twice and suspended in the same buffer, followed by cell disruption using a sonicator. Cell lysates were centrifuged at 13,000×g and 4° C. for 20 minutes to obtain only supernatants. Each enzyme was purified therefrom using His-tag affinity chromatography. The purified recombinant enzyme solution was dialyzed against 50 mM Tris-HCl (pH 8.0) buffer, and used for reaction.

A molecular weight of each purified enzyme was examined by SDS-PAGE, and as a result, it was confirmed that CT1 (α-glucan phosphorylase) has a molecular weight of about 96 kDa, CT2 (phosphoglucomutase) has a molecular weight of about 53 kDa, TN1 (glucose-6-phosphate-isomerase) has a molecular weight of about 51 kDa.

Example 3: Examination of Fructose-6-Phosphate-4-Epimerase Activity of Tagatose-Bisphosphate Aldolase 3-1. Production of Recombinant Expression Vector and Recombinant Microorganism Comprising Tagatose-Bisphosphate Aldolase Gene To identify a novel heat-resistant fructose-6-phosphate-4-epimerase, genetic information of tagatose-bisphosphate aldolase derived from *Kosmotoga olearia, Rhodothermus marinus, Rhodothermus profundi,* and *Limnochorda pilosa* which are thermophilic microorganisms was acquired to produce recombinant vectors expressible in *Escherichia.coli* and recombinant microorganisms.

In detail, a nucleotide sequence of tagatose-bisphosphate aldolase was selected from nucleotide sequences of *Kosmotoga olearia* or *Rhodothermus marinus* ATCC 43812, *Rhodothermus profundi* DSM 22212, and *Limnochorda pilosa* DSM 28787, which are registered in Genbank and KEGG (Kyoto Encyclopedia of Genes and Genomes), and based on information of amino acid sequences (SEQ ID NOS: 1, 3, 5 and 7) and nucleotide sequences (SEQ ID NOS: 2, 4, 6 and 8) of the four microorganisms, pBT7-C-His-CJ_KO_F6P4E, pBT7-C-His-CJ_RM_F6P4E, pBT7-C-His-CJ_RP_F6P4E, and pBT7-C-His-CJ_LP_F6P4E which are recombinant vectors comprising the nucleotide sequence of the enzyme and being expressible in *Escherichia.coli* were produced (Bioneer Corp., Korea).

Each of the produced expression vectors was transformed into *Escherichia.coli* BL21(DE3) by heat shock transformation (Sambrook and Russell: Molecular cloning, 2001) to produce recombinant microorganisms, and used after being frozen and stored in 50% glycerol. The recombinant microorganisms were designated as *Escherichia.coli* BL21(DE3)/ CJ_KO_F6P4E, *Escherichia.coli* BL21(DE3)/ CJ_RM_F6P4E, *Escherichia.coli* BL21(DE3)/ CJ_RP_F6P4E, and *Escherichia.coli* BL21(DE3)/ CJ_LP_F6P4E, respectively and deposited at the Korean Culture Center of Microorganisms (KCCM) which is an International Depositary Authority under the provisions of the Budapest Treaty with Accession Nos. KCCM11999P (date of deposit: Mar. 24, 2017), KCCM12096P (date of deposit: Aug. 11, 2017), KCCM12097P (date of deposit: Aug. 11, 2017), and KCCM12095P (date of deposit: Aug. 11, 2017), respectively.

To identify an additional novel heat-resistant fructose-6-phosphate-4-epimerase, a nucleotide sequence expected as the enzyme was selected from a nucleotide sequence of a thermophilic *Thermanaerothrix daxensis,* which is registered in Genbank, and based on information of an amino acid sequence (SEQ ID NO: 9) and a nucleotide sequence (SEQ ID NO: 10) of the microorganism, the gene was inserted into pBT7-C-His (Bioneer Corp.) which is a recombinant vector comprising the nucleotide sequence of the enzyme and being expressible in *Escherichia.coli* to produce a recombinant expression vector designated as pBT7-C-His-CJ_td1. The expression vector was transformed into an *Escherichia.coli* BL21(DE3) strain by a common transformation method [see Sambrook et al. 1989] to produce a transformant (transformed microorganism) designated as *Escherichia.coli* BL21(DE3)/pBT7-C-His-CJ_td1, and this transformant was deposited at the Korean Culture Center of Microorganisms (KCCM) under the provisions of the Budapest Treaty on Mar. 20, 2017 with Accession No. KCCM11995P (*Escherichia.coli* BL21(DE3)/pBT7-C-His-CJ_td1).

3-2. Production of Recombinant Tagatose-Bisphosphate Aldolase Enzyme

To produce recombinant enzymes, CJ_KO_F6P4E, CJ_RM_F6P4E, CJ_RP_F6P4E, CJ_LP_F6P4E, and CJ_TD1_F6P4E from the produced recombinant microorganisms, each of the recombinant microorganisms was seeded in a culture tube containing 5 ml of an LB liquid medium with ampicillin antibiotic, and then seed culture was performed in a shaking incubator at 37° C. until absorbance at 600 nm reached 2.0. Each of the cultures obtained by the seed culture was seeded in a culture flask containing an LB liquid medium, and then main culture was performed. When absorbance at 600 nm reached 2.0, 1 mM IPTG (isopropyl β-D-1-thiogalactopyranoside) was added to induce expression and production of the recombinant enzyme. The seed culture and the main culture were performed under conditions of 180 rpm and 37° C. Each culture of the main culture was centrifuged at 8,000×g and 4° C. for 20 minutes to recover cells. The recovered cells were washed with 25 mM Tris-HCl (pH 7.0) buffer twice and suspended in the same buffer, followed by cell disruption using a sonicator. Each cell lysate was centrifuged at 13,000×g and 4° C. for 20 minutes to take only a supernatant. The supernatant was purified using His-taq affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_2$PO$_4$ (pH 8.0) buffer containing 250 mM imidazole and 300 mM NaCl was further applied to perform elution and purification. Dialysis was performed using 25 mM Tris-HCl (pH 7.0) buffer to obtain CJ_KO_F6P4E, CJ_RM_F6P4E, CJ_RP_F6P4E, CJ_LP_F6P4E, and CJ_TD1_F6P4E which are purified enzymes for analysis of enzyme characterization.

3-3. Analysis of Fructose-6-Phosphate-4-Epimerase Activity of Recombinant Tagatose-Bisphosphate Aldolase Enzyme The fructose-6-phosphate-4-epimerase activities of the recombinant tagatose-bisphosphate aldolase enzymes obtained in Example 3-2 were analyzed. In detail, 1% by weight of fructose-6-phosphate as a substrate was suspended in 25 mM Tris-HCl (pH 7.0) buffer, and each 1 unit/ml of the purified CJ_KO_F6P4E, CJ_RM_F6P4E, CJ_RP_F6P4E, CJ_LP_F6P4E, and CJ_TD1_F6P4E was added thereto, and allowed to react at 60° C. for 1 hour. To remove phosphate, 1 unit/ml of phosphatase (Alkaline phosphatase of NEB, Calf Intestinal) was added and allowed to react at 37° C. for 1 hour. Reaction products were analyzed by HPLC, and HPLC analysis was performed under conditions of using a SP0810(Shodex) column and applying a mobile phase (water) at 80° C. and a flow rate of 1 ml/min, and resultants were analyzed using a refractive index detector.

As a result, it was confirmed that all of CJ_KO_F6P4E, CJ_RM_F6P4E, CJ_RP_F6P4E, and CJ_LP_F6P4E have the activity to convert fructose-6-phosphate into tagatose-6-phosphate (FIGS. 1A to 1D).

It was also confirmed that CJ_TD1_F6P4E has activity to convert fructose-6-phosphate into tagatose-6-phosphate (FIG. 5).

Example 4: Identification of Tagatose-6-Phosphate Phosphatase (D-Tagatose-6-Phosphate Phosphatase)

To perform production of tagatose from fructose-6-phosphate by simultaneous complex enzyme reactions in the tagatose production pathway of the present disclosure, tagatose-6-phosphate phosphatase which is able to exert the simultaneous enzyme reaction together with tagatose-bisphosphate aldolase was identified.

4-1. Production of Recombinant Expression Vector and Recombinant Microorganism Comprising Tagatose-6-Phosphate Phosphatase Gene A nucleotide sequence (SEQ ID NO: 12, hereinafter, referred to as t4) and an amino acid sequence (SEQ ID NO: 11) expected as the tagatose-6-phosphate phosphatase were selected from a nucleotide sequence of *Thermotoga maritima*, which is registered in Genbank, and based on the selected nucleotide sequence, a forward primer (SEQ ID NO: 33) and a reverse primer (SEQ ID NO: 34) were designed and synthesized. Polymerase chain reaction (PCR) was performed using the primers and genomic DNA of *Thermotoga maritima* as a template to amplify t4 gene. The amplified gene was inserted into pET21a (Novagen) which is a plasmid vector for expression in *Escherichia.coli* using restriction enzymes NdeI and XhoI, thereby producing a recombinant expression vector which was then designated as pET21a-CJ_t4. The produced expression vector was transformed into *Escherichia.coli* BL21(DE3) strain by heat shock transformation (Sambrook and Russell: Molecular cloning, 2001) to produce a recombinant microorganism, which was then used after being frozen and stored in 50% glycerol. The recombinant microorganism was designated as *Escherichia.coli* BL21(DE3)/pET21a-CJ_t4, and deposited at the Korean Culture Center of Microorganisms (KCCM) which is an International Depositary Authority under the provisions of the Budapest Treaty on Mar. 20, 2017 with Accession No. KCCM11994P.

4-2. Production of Recombinant Tagatose-6-Phosphate Phosphatase

*Escherichia.coli* BL21(DE3)/pET21a-CJ_t4 was seeded in a culture tube containing 5 ml of LB liquid medium and then seed culture was performed in a shaking incubator at 37° C. until absorbance at 600 nm reached 2.0. The culture obtained by the seed culture was seeded in a culture flask containing an LB liquid medium, and then main culture was performed. When absorbance at 600 nm reached 2.0, 1 mM IPTG was added to induce expression and production of the recombinant enzymes. The seed culture and the main culture were performed at a shaking speed of 180 rpm and 37° C. The culture obtained by the main culture was centrifuged at 8,000×g and 4° C. for 20 minutes to recover cells. The recovered cells were washed with 50 mM Tris-HCl (pH 8.0) buffer twice and suspended in the same buffer, followed by cell disruption using a sonicator. A cell lysate was centrifuged at 13,000×g and 4° C. for 20 minutes to obtain only a supernatant. The enzyme was purified therefrom using His-tag affinity chromatography. The purified enzyme was used after dialysis against 50 mM Tris-HCl (pH 8.0) buffer, and the purified recombinant enzyme was designated as CJ_T4.

4-3. Analysis of Tagatose-6-Phosphate Phosphatase Activity of CJ_T4

To analyze activity of CJ_T4, tagatose-6-phosphate was suspended in 50 mM Tris-HCl (pH 7.5) buffer, and 0.1 unit/ml of the purified CJ_T4 and 10 mM MgCl$_2$ were added thereto and allowed to react at 70° C. for 10 minutes. Then, the reaction product was analyzed by HPLC. HPLC analysis was performed under conditions of using a HPX-87H (Bio-Rad) column and applying a mobile phase (water) at 60° C. and a flow rate of 0.6 ml/min, and tagatose and tagatose-6-phosphate were analyzed using a refractive index detector.

As a result, tagatose was produced in the reaction product. As a result of performing the same reaction after adding CJ_T4 to phosphate and tagatose reactants, no tagatose was produced, indicating that CJ_T4 has irreversible tagatose-6-phosphate phosphatase activity (FIG. 3).

Example 5: Production of Tagatose by Simultaneous Complex Enzyme Reactions

1% (w/v) fructose-6-phosphate suspended in 25 mM Tris-HCl (pH 7.0) buffer was added to a mixed enzyme solution of 1 unit/ml of CJ_KO_F6P4E or CJ_RP_F6P4E and 1 unit/ml of CJ_t4 (Accession No. KCCM11994P), and allowed to react at 60° C. for 1 hour, and then HPLC was performed to analyze the reaction product. HPLC analysis was performed under conditions of using a SP0810 (Shodex) column and applying a mobile phase (water) at 80° C. and a flow rate of 1 ml/min, and tagatose was detected using a refractive index detector.

As a result, tagatose production was observed, indicating that tagatose may be produced from fructose-6-phosphate by simultaneous complex enzyme reactions of tagatose-bisphosphate aldolase and tagatose-6-phosphate phosphatase (FIGS. 2A and 2B).

Example 6: Production of Tagatose from Maltodextrin by Simultaneous Complex Enzyme Reactions To analyze the activity to produce tagatose from maltodextrin by complex enzymes, 5% (w/v) maltodextrin was added to a reaction solution containing 1 unit/ml of CT1, 1 unit/ml of CT2, 1 unit/ml of TN1, 1 unit/ml of T4, 1 unit/ml of TD1, 20 mM to 50 mM of sodium phosphate (pH 7.0), and allowed to react at 60° C. for 1 hour, and then HPLC was performed to analyze the reaction product. HPLC analysis was performed under conditions of using a SP0810 (Shodex) column and applying a mobile phase (water) at 80° C. and a flow rate of 0.6 ml/min, and tagatose was detected using a refractive index detector.

As a result, it was confirmed that tagatose may be produced from maltodextrin by the complex enzyme reactions of added CT1, CT2, TN1, T4, and TD1 (FIG. 6).

Effect of the Invention

A method of producing tagatose according to the present disclosure is economical because of using glucose or starch as a raw material, accumulates no phosphate to achieve a high conversion rate, and comprises a tagatose-6-phosphate phosphatase reaction which is an irreversible reaction pathway, thereby remarkably increasing a conversion rate into tagatose.

Further, tagatose may be produced from glucose or starch as a raw material by complex enzyme reactions, and thus there are advantages that the method is simple and economical, and a yield is improved.

International Depositary Authority: Korean Culture Center of Microorganisms (foreign)
Accession No: KCCM11990P
Date of deposit: 2017 Mar. 20
International Depositary Authority: Korean Culture Center of Microorganisms (foreign)
Accession No: KCCM11991P
Date of deposit: 2017 Mar. 20
International Depositary Authority: Korean Culture Center of Microorganisms (foreign)
Accession No: KCCM11992P
Date of deposit: 2017 Mar. 20
International Depositary Authority: Korean Culture Center of Microorganisms (foreign)
Accession No: KCCM11993P
Date of deposit: 2017 Mar. 20
International Depositary Authority: Korean Culture Center of Microorganisms (foreign)
Accession No: KCCM11994P
Date of deposit: 2017 Mar. 20
International Depositary Authority: Korean Culture Center of Microorganisms (foreign)
Accession No: KCCM11995P
Date of deposit: 2017 Mar. 20
International Depositary Authority: Korean Culture Center of Microorganisms (foreign)
Accession No: KCCM11999P
Date of deposit: 2017 Mar. 24
International Depositary Authority: Korean Culture Center of Microorganisms (foreign)
Accession No: KCCM12096P
Date of deposit: 2017 Aug. 11
International Depositary Authority: Korean Culture Center of Microorganisms (foreign)
Accession No: KCCM12097P
Date of deposit: 2017 Aug. 11
International Depositary Authority: Korean Culture Center of Microorganisms (foreign)
Accession No: KCCM12095P
Date of deposit: 2017 Aug. 11

What is claimed is:

1. A method of producing tagatose, comprising:
   (a) producing tagatose-6-phosphate by contacting fructose-6-phosphate with tagatose-6-phosphate kinase, a microorganism expressing the tagatose-6-phosphate kinase, or a culture of the microorganism, wherein the tagatose-6-phosphate kinase consists of the amino acid sequence of SEQ ID NO: 3 or 5; and
   (b) producing tagatose by contacting the produced tagatose-6-phosphate with tagatose-6-phosphatase, a microorganism expressing the tagatose-6-phosphate phosphatase, or a culture of the microorganism.

2. The method of claim 1, further comprising converting glucose-6-phosphate into fructose-6-phosphate by contacting glucose-6-phosphate with glucose-6-phosphate-isomerase, a microorganism expressing the glucose-6-phosphate-isomerase, or a culture of the microorganism.

3. The method of claim 2, further comprising converting glucose-1-phosphate into glucose-6-phosphate by contacting glucose-1-phosphate with phosphoglucomutase, a microorganism expressing the phosphoglucomutase, or a culture of the microorganism.

4. The method of claim 3, further comprising converting starch, maltodextrin, or sucrose into glucose-1-phosphate by contacting starch, maltodextrin, sucrose, or a combination thereof with α-glucan phosphorylase, starch phosphorylase, maltodextrin phosphorylase, or sucrose phosphorylase, a microorganism expressing the α-glucan phosphorylase, starch phosphorylase, maltodextrin phosphorylase, or sucrose phosphorylase, or a culture of the microorganism.

5. The method of claim 2, further comprising converting glucose into glucose-6-phosphate by contacting glucose with glucokinase, a microorganism expressing the glucokinase, or a culture of the microorganism.

6. The method of claim 5, further comprising convening starch, maltodextrin or sucrose into glucose by contacting starch, maltodextrin, sucrose, or a combination thereof with α-amylase, pullulanase, glucoamylase, sucrase, or isoamylase, a microorganism expressing the α-amylase, pullulanase, glucoamylase, sucrose, or isoamylase, or a culture of the microorganism.

7. The method of claim 1, wherein the contacting is performed at pH 5.0 to 9.0, 40° C. to 80° C., or for 0.5 hours to 24 hours.

8. A method of producing tagatose, comprising contacting (a) starch, maltodextrin, sucrose, or a combination thereof; with (b) (i) tagatose-6-phosphate phosphatase, (ii) tagatose-6-phosphate kinase consists of the amino acid sequence of SEQ ID NO: 3 or 5, (iii) glucose-6-phosphate-isomerase, (iv) phosphoglucomutase or glucokinase, (v) phosphorylase, and (vi) one or more of α-amylase, pullulanase, isoamylase, glucoamylase, or sucrase; and (c) phosphate.

* * * * *

SEQUENCE LISTING

```
<160> NUMBER OF SEQ ID NOS: 30

<210> SEQ ID NO 1
<211> LENGTH: 429
<212> TYPE: PRT
<213> ORGANISM: Artificial Sequence
<220> FEATURE:
<223> OTHER INFORMATION: Fructose-6-phosphate C4 epimerase derived from
      Anaerolinea thermophila (AN1)

<400> SEQUENCE: 1

Met Met Phe Gly Ser Pro Ala Pro Leu Leu Asp Met Val Thr Ala Gln
1               5                   10                  15

Lys Gln Gly Met Ala Arg Gly Ile Pro Ser Ile Cys Ser Ala His Pro
            20                  25                  30

Val Val Leu Ser Ala Ala Cys His Leu Ala Arg Arg Ser Gly Ala Pro
        35                  40                  45

Leu Leu Ile Glu Thr Thr Cys Asn Gln Val Asn His Gln Gly Gly Tyr
    50                  55                  60

Ser Gly Met Thr Pro Ala Asp Phe Val Arg Phe Leu Arg Glu Ile Leu
65                  70                  75                  80

Glu Arg Glu Gly Ile Pro Pro Gln Gln Val Ile Leu Gly Gly Asp His
                85                  90                  95

Leu Gly Pro Tyr Pro Trp Arg Lys Glu Pro Ala Glu Thr Ala Ile Ala
            100                 105                 110

Gln Ala Leu Glu Met Val Arg Ala Tyr Val Gln Ala Gly Tyr Thr Lys
        115                 120                 125
```

```
Ile His Leu Asp Ala Ser Met Pro Cys Ala Asp Asp Pro Glu Arg
    130                 135                 140

Pro Leu Pro Leu Glu Arg Ile Ala Arg Arg Ala Ala Gln Leu Cys Ala
145                 150                 155                 160

Ala Ala Glu Ala Ala Ala Gly Ala Val Gln Pro Val Tyr Val Ile Gly
                165                 170                 175

Ser Glu Val Pro Pro Gly Gly Ala Gln Gly Gln Glu Ala Arg Leu
            180                 185                 190

His Val Thr Thr Pro Gln Glu Ala Gln Ala Ala Leu Asp Ala Phe Arg
        195                 200                 205

Glu Ala Phe Leu Gln Ala Gly Leu Thr Pro Val Trp Glu Arg Val Ile
210                 215                 220

Ala Leu Val Val Gln Pro Gly Val Glu Phe Gly Val Asp Ser Ile His
225                 230                 235                 240

Ala Tyr Gln Arg Glu Ala Ala Arg Pro Leu Lys Thr Phe Ile Glu Gly
                245                 250                 255

Val Pro Gly Met Val Tyr Glu Ala His Ser Thr Asp Tyr Gln Thr Arg
            260                 265                 270

Ala Ser Leu Arg Ala Leu Val Glu Asp His Phe Ser Ile Leu Lys Val
        275                 280                 285

Gly Pro Ala Leu Thr Phe Ala Tyr Arg Glu Ala Val Phe Ala Leu Glu
290                 295                 300

His Ile Glu Arg Glu Ile Leu Gly Arg Gln Asp Met Pro Leu Ser Arg
305                 310                 315                 320

Leu Ser Glu Val Leu Asp Glu Val Met Leu Asn Asp Pro Arg His Trp
                325                 330                 335

Gln Gly Tyr Phe Ala Gly Ala Pro Ala Glu Gln Ala Leu Ala Arg Arg
            340                 345                 350

Tyr Ser Phe Ser Asp Arg Ile Arg Tyr Tyr Trp His His Pro Ala Ala
        355                 360                 365

Gln Glu Ala Val Arg Arg Leu Leu Ala Asn Leu Ile Glu Thr Pro Pro
370                 375                 380

Pro Leu Ser Leu Leu Ser Gln Tyr Leu Pro Arg Glu Tyr Glu Met Val
385                 390                 395                 400

Arg Ala Gly Glu Ile Ser Ser His Pro Gln Asp Leu Ile Arg Ala His
                405                 410                 415

Ile Gln His Thr Leu Glu Asp Tyr Ala Ala Ala Cys Gly
            420                 425
```

<210> SEQ ID NO 2
<211> LENGTH: 1278
<212> TYPE: DNA
<213> ORGANISM: Artificial Sequence
<220> FEATURE:
<223> OTHER INFORMATION: DNA sequence of Fructose-6-phosphate C4 epimerase derived from Anaerolinea thermophila (AN1)

<400> SEQUENCE: 2

```
atgaccgcca tttttggaaaa tctcgccgcc gcgcgccgcg ccggcaaacc tgcgggcatc      60
acttcggtct gctcggccca cccgttgtc ctgcgcgccg caatccgccg cgccgccgcc     120
agtcaaacgg ccgtactgat cgaggccacc tgcaatcagg tcaatcatct cggtggttat     180
accggcatga caccgcgtga cttcgttgcc ttcgtcaaca gcatcgccgc ggaagaagga     240
ctgcccgccg aactgctgat cttggcgg gatcatctcg ccccaatcc ctggcgcagg      300 gagaaggccg aggacgcgct gacaaaagcc gccgccatgg tcgacgccta tgtcacagct     360
```

```
ggttttcgca agatccacct tgatgcatcg atgggctgcg ccggtgagcc ggcagccctg    420
gatgacgtca ccatcgccca ccgcgccgcg aaactcacag ccgttgccga aaaggcagcc    480
actgaggctg gcctgccaaa accgctttat attctgggca ccgaagtgcc ggtgccggc     540 ggtgccgacc atgtgcttga ccgtcgca ccgaccgaac gcaggcggc gcaacacc         600 atcgatcttc atcgcgaaat ctttgcgcag cacggtcttt ccgatgcgtt cgaacgggtc    660
atcgcctttg tcgtgcagcc gggtgtggaa ttcggcagcg acaatgtcgt cgcttatgat    720
ccgcaggcag cgcagagcct gagcgccgtg ctggatggcg aaccgcgact ggtcttcgaa    780
gcccattcga ccgattacca gaccgagcct gcccttgcgg cactggtacg cgacggatat    840
ccgatcctca aagttggacc gggcctcacc ttcgcttacc gggaagcgct ttatgcactc    900
gacatgatcg cctccgaaat ggtcggcacc tatggcgacc gaccgctggc gcggactatg    960
gaaaaattga tgttaagcgc gccgggcgac tggcagggcc attaccatgg cgacgacatc   1020
acgctccgat tgcaacgcca ttacagctac agcgaccgca tccgttacta ctggacgcga   1080
ccggaagcgc tcgcggccgt ttccaccttg cataaggcac tggatgggaa gacaattccc   1140
gaaaccctgc tgcgccaata tctcggcgaa ttgccgctcg cggcggttgc gggaaaggaa   1200
ccggaggagg ttctggtcgc ggcggtggat caggtgctgg cgacctatca cgcggcgacg   1260
ggcgaaggcc gccactga                                                 1278
```

<210> SEQ ID NO 3
<211> LENGTH: 443
<212> TYPE: PRT
<213> ORGANISM: Artificial Sequence
<220> FEATURE:
<223> OTHER INFORMATION: Amino acid sequences of CJ_AB_F6P4E derived
      from Anaerolineae bacterium

<400> SEQUENCE: 3

```
Met Thr Arg Asn Ser Pro Leu Ser Glu Val Ile Ala Ala Gln Lys Arg
1               5                  10                  15

Gly Glu Ser Arg Gly Ile Ala Ser Ile Cys Ser Ala Asn Pro Trp Val
            20                  25                  30

Ile Glu Ala Met Leu Gln Gln Ala Arg Ala Thr Gly Glu Pro Val Leu
        35                  40                  45

Ile Glu Ser Thr Cys Asn Gln Val Asn Gln Phe Gly Gly Tyr Thr Gly
    50                  55                  60

Trp Thr Pro Asp Gln Phe Met Ala Tyr Leu Arg Asp Leu Ala Pro Arg
65                  70                  75                  80

Gln Glu Phe Pro Phe Asp His Ile Ile Val Gly Gly Asp His Leu Gly
                85                  90                  95

Pro Ser Pro Trp Gln Asp Glu Pro Ala Ala Ile Ala Met Asp Lys Ala
            100                 105                 110

Lys Ile Leu Ile Arg Asp Cys Val Arg Ala Gly Tyr Thr Lys Ile His
        115                 120                 125

Leu Asp Ala Ser Met Lys Cys Ala Asp Asp Pro His Arg Pro Leu
    130                 135                 140

Asp Thr Arg Ile Ser Ala Ala Arg Ala Ala Glu Leu Ala Gln Val Ala
145                 150                 155                 160

Glu Lys Ala Phe Ser Glu His Pro Pro Gly Gly Ala Pro Pro Tyr Tyr
                165                 170                 175

Val Ile Gly Thr Glu Val Pro Leu Pro Gly Gly Val Gln Glu Gln Glu
            180                 185                 190
```

Glu Gly Leu Ser Val Thr Ser Ile Gly Asp Val Ala Gly Thr Ile Glu
            195                 200                 205

Ser Thr Lys Glu Ala Phe Phe Ala Arg Gly Leu Glu Arg Ala Trp Glu
    210                 215                 220

Arg Val Ile Ala Val Val Val Gln Pro Gly Val Glu Tyr Gly Asp Ala
225                 230                 235                 240

Thr Leu Phe Glu Tyr Asp Arg Ala Arg Ala Asp Leu Ala Arg Phe
                245                 250                 255

Ile Glu Gly Tyr Asp Gly Leu Ile Tyr Glu Ala His Ser Thr Asp Tyr
                260                 265                 270

Gln Leu Ala Glu Ala Leu Arg Gln Leu Val Glu Asp His Phe Ala Ile
            275                 280                 285

Leu Lys Val Gly Pro Ala Leu Thr Phe Ser Phe Arg Glu Gly Val Phe
            290                 295                 300

Ala Leu Ala Ala Ile Glu Glu Glu Leu Leu Ala Gly Arg Gln Asp Val
305                 310                 315                 320

Glu Pro Ser Arg Val Arg Glu Val Leu Asp Lys Thr Met Leu Ala Asn
                325                 330                 335

Pro Ile Tyr Trp Gln Lys Tyr Tyr Gln Gly Asp Gln Ala Val His
            340                 345                 350

Leu Lys Arg Lys Tyr Ser Phe Ser Asp Arg Ser Arg Tyr Tyr Trp Pro
            355                 360                 365

Val Pro Glu Val Gln Phe Ser Leu Ser Arg Leu Ile Gln Asn Leu Gly
            370                 375                 380

Glu Gln Pro Leu Pro Leu Thr Leu Leu Ser Gln Tyr Leu Pro Val Gln
385                 390                 395                 400

Tyr Ala Arg Ile Arg Gly Gly Glu Ile Ala Asn Val Pro Arg Ala Ile
                405                 410                 415

Leu Leu Asp Lys Val Arg Ser Val Leu Ser Asp Tyr Ser Tyr Ala Cys
            420                 425                 430

Gly Tyr Leu Thr Gly Pro Ala Arg Arg Asn Arg
            435                 440

<210> SEQ ID NO 4
<211> LENGTH: 1332
<212> TYPE: DNA
<213> ORGANISM: Artificial Sequence
<220> FEATURE:
<223> OTHER INFORMATION: Nucleotide sequence of CJ_AB_F6P4E

<400> SEQUENCE: 4
atgactcgga actcgccctt atcagaggtg atcgctgccc agaaacgcgg cgagagcaga     60
gggatcgctt ccatatgctc ggccaatccc tgggtcatcg aggccatgct gcaacaggcc    120
cgcgcgaccg gcgaacctgt cctgatcgag tcgacctgca accaggtcaa tcaattcggc    180
ggctacaccg gttggacgcc ggatcaattc atggcctatc ttcgagattt ggcgccccgg    240
caagaatttc cctttgacca catcatcgtc ggcggcgatc atctcgggcc tagcccctgg    300
caagacgagc cggccgcgat agcgatggat aaggccaaga tcctgatccg ggattgcgtc    360
cgggcaggtt acaccaagat tcacctggac gccagcatga gtgcgccga cgacgatccc    420 catcggccgc tagataccag gatatctgcg gcccgggcgg ccgagctggc ccaggtggcc    480
gaaaaagcat tctccgagca cccaccaggc ggtgcgccgc ttattatgt gatcggcacc    540 gaggtgccct tgcccggtgg ggttcaggaa caggaggagg gattgagtgt taccagtata    600

-continued

```
ggcgacgtgg ccggaaccat tgaatcgacc aaagaagcct tttttgcacg aggcttagaa    660
agggcttggg aacgggtcat agccgtcgtg gtgcaacccg gcgtggagta tggtgatgcc    720
acgttatttg aatatgatcg ggctcgggcg gccgatctgg cccgatttat cgaaggttat    780
gatggcttga tatacgaagc gcattccact gattatcagt tagctgaggc actccggcag    840
ttggtagaag atcatttcgc catcttgaag gtggggccag cgctaacatt ttcatttcgg    900
gagggggttt ttgccctggc tgccatagaa gaggagctgt tggccgggcg acaggatgtc    960
gaaccgtcac gggtgcgcga agttctggat aagaccatgt tggctaatcc aatctactgg   1020
cagaagtatt atcagggaga tgaccaggcc gtacatttga aaaggaaata tagttttagt   1080
gaccgttccc gatactattg gccggttccc gaggtgcaat tttctttgtc ccgactaatt   1140
caaaatttgg gagagcagcc gctgcctcta acgctcttaa gccaataccT gccggtccaa   1200
tacgcccgaa tcagaggtgg cgaaatagcc aatgttcccc gggcgatcct cttggataag   1260
gtcagaagcg tactctctga ttactcatat gcatgcggtt atctgaccgg ccctgctaga   1320
agaaaccgct ga                                                       1332
```

<210> SEQ ID NO 5
<211> LENGTH: 408
<212> TYPE: PRT
<213> ORGANISM: Artificial Sequence
<220> FEATURE:
<223> OTHER INFORMATION: Amino acid sequences of CJ_DT_F6P4E derived
      from Dictyoglomus thermophilum

<400> SEQUENCE: 5

```
Met Trp Leu Ser Lys Asp Tyr Leu Arg Lys Lys Gly Val Tyr Ser Ile
1               5                   10                  15

Cys Ser Ser Asn Ser Tyr Val Ile Glu Ala Ser Ile Glu Phe Ala Lys
            20                  25                  30

Glu Lys Gly Asp Tyr Ile Leu Ile Glu Ala Thr Pro His Gln Val Asn
        35                  40                  45

Gln Phe Gly Gly Tyr Ser Gly Met Thr Pro Glu Asp Phe Lys Asn Phe
    50                  55                  60

Val Met Lys Ile Ala Lys Glu Lys Gly Leu Glu Glu Asp Lys Ile Ile
65                  70                  75                  80

Leu Gly Gly Asp His Leu Gly Pro Leu Pro Trp Gln Asp Glu Pro Ser
                85                  90                  95

Pro Thr Ala Met Asn Lys Ala Lys Asp Leu Ile Arg Ala Phe Val Glu
            100                 105                 110

Ser Gly Tyr Lys Lys Ile His Ile Asp Cys Ser Met Pro Leu Ser Asp
        115                 120                 125

Asp Pro Lys Val Leu Pro Tyr Glu Lys Ile Ala Glu Arg Thr Arg Glu
    130                 135                 140

Leu Phe Glu Ile Ala Glu Glu Thr Ala Arg Lys Tyr Asn Phe Gln Pro
145                 150                 155                 160

Val Tyr Val Val Gly Thr Asp Val Pro Ile Ala Gly Gly Gly Glu Glu
                165                 170                 175

Glu Gly Val Thr Ser Val Glu Asp Phe Arg Ser Ala Ile Ser Ser Leu
            180                 185                 190

Lys Lys Tyr Phe Asn Asp Val Pro Asn Ile Trp Asp Arg Val Val Gly
        195                 200                 205

Phe Val Ile Met Leu Gly Ile Gly Phe Ser Tyr Asp Lys Val Phe Glu
    210                 215                 220
```

```
Tyr Asp Arg Asp Lys Val Arg Gly Ile Leu Glu Glu Val Lys Arg Glu
225                 230                 235                 240

Asp Leu Phe Val Glu Gly His Ser Thr Asp Tyr Gln Ala Arg Tyr Ala
            245                 250                 255

Leu Arg Asn Met Val Glu Asp Gly Val Arg Ile Leu Lys Val Gly Pro
        260                 265                 270

Ala Leu Thr Ala Ala Phe Arg Arg Gly Val Phe Leu Leu Ser Asn Ile
        275                 280                 285

Glu Asp Glu Ile Ile Pro Glu Arg Glu Arg Ser Asn Ile Lys Arg Val
        290                 295                 300

Ile Leu Glu Thr Met Leu Arg Asp Asp Arg Tyr Trp Arg Lys Tyr Tyr
305                 310                 315                 320

Lys Asp Ser Lys Arg Leu Glu Leu Asp Ile Trp Tyr Asn Leu Leu Asp
            325                 330                 335

Arg Ile Arg Tyr Tyr Trp Glu Tyr Glu Asp Val Lys Met Val Leu Asn
                340                 345                 350

Lys Leu Phe Glu Asn Phe Ser Glu Gly Val Asp Ile Lys Phe Ile Tyr
        355                 360                 365

Gln Tyr Phe Tyr Asp Ser Tyr Phe Asp Val Arg Glu Gly Lys Met Lys
370                 375                 380

Asn Asp Pro Arg Glu Leu Ile Lys Lys Glu Ile Lys Arg Val Leu Glu
385                 390                 395                 400

Asp Tyr Ser Tyr Ala Ile Asn Leu
                405

<210> SEQ ID NO 6
<211> LENGTH: 1227
<212> TYPE: DNA
<213> ORGANISM: Artificial Sequence
<220> FEATURE:
<223> OTHER INFORMATION: Nucleotide sequence of CJ_DT_F6P4E derived from
      Dictyoglomus thermophilum

<400> SEQUENCE: 6
atgtggctaa gcaaagatta ccttaggaaa aagggagttt attctatatg cagttctaat     60
tcttatgtga ttgaggcaag tattgaattt gctaaggaaa aggtgattat atcctgatt    120 gaagcaactc ctcatcaagt gaatcagttt ggtggatatt caggaatgac tcctgaagat    180
tttaaaaatt ttgtaatgaa gatagcaaag gaaaaggggt tggaagaaga taagataatt    240 cttgggggg atcatttagg tccccttcct tggcaagatg aaccttcacc aacagcaatg    300
aataaggcga aggatcttat cagggctttc gtggaaagtg gctataagaa gatacatatt    360
gattgtagta tgcctctttc cgatgatcct aaagtgcttc cttatgaaaa aatagcagaa    420
agaacaagag agctttttga aattgccgaa gagactgcaa gaaaatataa ttttcagcct    480
gtatatgtgg taggaactga tgtgcctata gcaggaggtg gtgaagaaga aggagtaact    540
tctgtagagg attttagatc tgcaatctct tcattaaaga aatatttaa tgatgtccct    600 aatatatggg atagagtagt aggttttgta ataatgcttg gtataggatt tagttatgat    660
aaagtatttg aatatgatag ggataaagtg agaggtatat tggaagaggt gaaaagagaa    720
gacttatttg tagagggtca ttctaccgat taccaagcaa gatatgcatt aagaaatatg    780
gtagaagatg gagtaagaat tctgaaggtg gtcctgcttt aactgcagcc tttagaaga    840 ggagttttct tgcttagtaa tattgaggat gaaattatac ctgaaaggga agatctaat    900 ataaagagag tcatacttga acaatgcta agggatgata gatattggag aaagtattat    960
```

-continued

```
aaggattcga agaggttaga attagacatt tggtataact tattggatag aattaggtat    1020
tattgggagt atgaggatgt aaaaatggtt ttaaacaagc ttttgaaaa cttttcagag    1080 ggtgttgata ttaagtttat atatcaatat ttttatgatt catattttga tgtgagagaa    1140
ggaaaaatga agaatgatcc aagagaactt ataaaaaaag agataaaaag agttttggag    1200
gattatagct atgctataaa cttataa                                       1227
```

<210> SEQ ID NO 7
<211> LENGTH: 263
<212> TYPE: PRT
<213> ORGANISM: Artificial Sequence
<220> FEATURE:
<223> OTHER INFORMATION: Tagatose-6-phosphate phosphatase derived from
      Thermotoga maritima (T4)

<400> SEQUENCE: 7

```
Met Glu Gly Gly Ile Glu Leu Asp Arg Leu Asp Phe Ser Ile Lys Leu
1               5                   10                  15

Leu Arg Arg Val Gly His Phe Leu Met Leu His Trp Gly Lys Val Asp
            20                  25                  30

Ser Val Glu Lys Lys Thr Gly Phe Lys Asp Ile Val Thr Glu Ile Asp
        35                  40                  45

Lys Lys Ala Gln Glu Met Ile Val Glu Ile Arg Lys Val Phe Pro
    50                  55                  60

Asp Glu Asn Ile Ile Ala Glu Gly Ile Ser Glu Asn Gly Lys Lys
65                  70                  75                  80

Leu Trp Ile Ile Asp Pro Ile Asp Gly Thr Ile Asn Phe Val His Gly
                85                  90                  95

Leu Pro Asn Phe Ser Ile Ser Ile Ala Tyr Val Glu Asn Gly Glu Val
            100                 105                 110

Lys Met Gly Val Val His Ala Pro Ala Leu Asn Glu Thr Leu Tyr Ala
        115                 120                 125

Glu Glu Asn Gly Gly Ala Phe Leu Asn Gly Glu Arg Ile Arg Val Ser
    130                 135                 140

Gly Asn Thr Ser Leu Glu Glu Cys Val Gly Ser Thr Gly Ser Tyr Val
145                 150                 155                 160

Asp Phe Thr Gly Lys Phe Ile Glu Lys Met Glu Lys Lys Thr Arg Arg
                165                 170                 175

Val Arg Ile Leu Gly Ser Ala Ala Leu Asn Ala Cys Tyr Val Gly Ala
            180                 185                 190

Gly Arg Val Asp Phe Phe Val Thr Trp Arg Ile Asn Pro Trp Asp Ile
        195                 200                 205

Ala Ala Gly Leu Ile Val Val Lys Glu Ala Gly Gly Thr Val Thr Asp
    210                 215                 220

Phe Ala Gly Lys Glu Ala Asn Val Phe Ser Lys Asn Phe Val Phe Ser
225                 230                 235                 240

Asn Gly Leu Val His Glu Glu Val Leu Glu Val Val Asn Glu Val Leu
                245                 250                 255

Lys Glu Ile Gly Glu Gly Lys
            260
```

<210> SEQ ID NO 8
<211> LENGTH: 792
<212> TYPE: DNA
<213> ORGANISM: Artificial Sequence
<220> FEATURE:
<223> OTHER INFORMATION: DNA sequence of tagatose-6-phosphate phosphatase derived from Thermotoga maritima (T4)

<400> SEQUENCE: 8

```
atggaggag ggatcgaatt ggacagactg gactttcga taaaactcct gagaagggtt      60
gggcacttc tcatgcttca ctggggaaag gtggacagtg tggagaaaaa gaccggttc     120
aaagacatcg tgacggaaat agacaaaaag gcccaggaga tgatagtgga ggagatcaga    180
aaggttttc cggatgagaa cataatagcg gaggaggga tctcggagaa cggaaaaaaa     240
ctctggataa tagatcccat agacgggacg ataaacttcg ttcatggact tcccaacttt    300
tccatctcca tcgcttacgt ggagaatgga gaggtgaaga tgggagttgt gcacgctcct    360
gcactcaacg aaacactcta cgccgaagaa acgggggtg ctttttttgaa cggtgaaagg    420
atcagggtgt ctggaaacac aagtcttgaa gagtgcgtgg gatcaacggg aagctatgtg    480
gatttcaccg gaagtttat cgagaagatg gaaaagaaaa caaggagagt gagaattctg    540
gggagtgcgg cgctgaacgc ctgctacgtg ggagcaggga gggtggattt cttcgtcact    600
tggaggatca atccgtggga catcgcagca ggcctgatag ttgtgaaaga ggcgggagga    660
acggtgacag attttgccgg aaaagaggca acgttttct cgaagaattt tgtcttctcc    720
aacggactcg ttcacgaaga agttctcgaa gtggtgaacg aggttctgaa agagatagga    780
gaggggaagt ga                                                         792
```

<210> SEQ ID NO 9
<211> LENGTH: 451
<212> TYPE: PRT
<213> ORGANISM: Artificial Sequence
<220> FEATURE:
<223> OTHER INFORMATION: glucose-6-phosphate isomerase derived from Thermotoga maritima (TN1)

<400> SEQUENCE: 9

```
Met Lys Lys Met Ala Leu Lys Phe Asp Phe Ser Asn Leu Phe Glu Pro
1               5                   10                  15

Asn Ile Ser Gly Gly Leu Arg Glu Glu Asp Leu Glu Ser Thr Lys Glu
            20                  25                  30

Lys Val Ile Glu Ala Ile Lys Asn Phe Thr Glu Asn Thr Pro Asp Phe
        35                  40                  45

Ala Arg Leu Asp Arg Lys Trp Ile Asp Ser Val Lys Glu Leu Glu Glu
    50                  55                  60

Trp Val Val Asn Phe Asp Thr Val Val Leu Gly Ile Gly Gly Ser
65                  70                  75                  80

Gly Leu Gly Asn Leu Ala Leu His Tyr Ser Leu Arg Pro Leu Asn Trp
                85                  90                  95

Asn Glu Met Ser Arg Glu Glu Arg Asn Gly Tyr Ala Arg Val Phe Val
            100                 105                 110

Val Asp Asn Val Asp Pro Asp Leu Met Ala Ser Val Leu Asp Arg Ile
        115                 120                 125

Asp Leu Lys Thr Thr Leu Phe Asn Val Ile Ser Lys Ser Gly Ser Thr
    130                 135                 140

Ala Glu Val Met Ala Asn Tyr Ser Ile Ala Arg Gly Ile Leu Glu Ala
145                 150                 155                 160

Asn Gly Leu Asp Pro Lys Glu His Ile Leu Ile Thr Thr Asp Pro Glu
                165                 170                 175

Lys Gly Phe Leu Arg Lys Val Val Lys Glu Glu Gly Phe Arg Ser Leu
            180                 185                 190
```

```
Glu Val Pro Pro Gly Val Gly Arg Phe Ser Val Leu Thr Pro Val
            195                 200                 205

Gly Leu Phe Ser Ala Met Ala Glu Gly Ile Asp Ile Glu Leu His
    210                 215                 220

Asp Gly Ala Arg Asp Ala Phe Glu Arg Cys Lys Lys Glu Asp Leu Phe
225                 230                 235                 240

Glu Asn Pro Ala Ala Met Ile Ala Leu Thr His Tyr Leu Tyr Leu Lys
                245                 250                 255

Arg Gly Lys Ser Ile Ser Val Met Met Ala Tyr Ser Asn Arg Met Thr
            260                 265                 270

Tyr Leu Val Asp Trp Tyr Arg Gln Leu Trp Ala Glu Ser Leu Gly Lys
        275                 280                 285

Arg Tyr Asn Leu Lys Gly Glu Glu Val Phe Thr Gly Gln Thr Pro Val
290                 295                 300

Lys Ala Ile Gly Ala Thr Asp Gln His Ser Gln Ile Gln Leu Tyr Asn
305                 310                 315                 320

Glu Gly Pro Asn Asp Lys Val Ile Thr Phe Leu Arg Leu Glu Asn Phe
                325                 330                 335

Asp Arg Glu Ile Ile Ile Pro Asp Thr Gly Arg Glu Glu Leu Lys Tyr
            340                 345                 350

Leu Ala Arg Lys Arg Leu Ser Glu Leu Leu Leu Ala Glu Gln Thr Gly
        355                 360                 365

Thr Glu Glu Ala Leu Arg Lys Asn Asp Arg Pro Asn Met Lys Val Ile
370                 375                 380

Phe Asp Arg Leu Thr Ser Tyr Asn Val Gly Gln Phe Phe Ala Tyr Tyr
385                 390                 395                 400

Glu Ala Ala Thr Ala Phe Met Gly Tyr Leu Leu Glu Ile Asn Pro Phe
                405                 410                 415

Asp Gln Pro Gly Val Glu Leu Gly Lys Lys Ile Thr Phe Ala Leu Met
            420                 425                 430

Gly Arg Glu Gly Tyr Glu Tyr Glu Ile Lys Asp Arg Thr Lys Lys Val
        435                 440                 445

Ile Ile Glu
    450

<210> SEQ ID NO 10
<211> LENGTH: 1356
<212> TYPE: DNA
<213> ORGANISM: Artificial Sequence
<220> FEATURE:
<223> OTHER INFORMATION: DNA sequence of glucose-6-phosphate isomerase
      derived from Thermotoga maritima (TN1)

<400> SEQUENCE: 10
atgaaaaaga tggctttgaa atttgatttt tcaaatcttt ttgaaccgaa catctccggt    60
ggactgagag aggaagatct ggaaagcaca aaagaaaagg tgatagaggc gataaagaat   120
ttcactgaga acacaccgga ttttgccaga ctggacagaa atggatcga ttcggtgaag    180 gaactcgagg agtgggtggt gaacttcgac acggtggtcg ttctgggaat tggggatcc    240 ggtcttggaa accttgccct tcattattcg ttgagaccac tgaactggaa cgagatgtcg   300
agagaggaaa gaaacggtta tgcgagagtc ttcgtggtgg acaacgtaga tcccgatctc   360
atggcctccg tccttgatag gatagatctg aagacaacgc tgttcaacgt gatctcaaaa   420
tctggatcca cggctgaggt tatggcgaat tactcgatcg caaggggaat cctggaggct   480
aatggtctgg acccgaaaga acacatcctc atcacaacag atccagagaa gggcttttg    540
```

```
agaaaagtag tgaaagaaga gggcttcaga agtcttgagg tccctcccgg cgttggagga    600
aggttcagcg tgctgacgcc cgttggcctc ttctctgcca tggcggaggg tatcgacata    660
gaagaactcc acgacggtgc ccgggatgcg ttcgagagat gcaagaagga agacctgttc    720
gaaaatccag cggcgatgat cgccctcaca cactatctct atctgaagag aggaaagagc    780
atctccgtca tgatggccta ctccaacagg atgacctacc tcgtggactg gtacagacag    840
ctgtgggcag aaagtctggg aaagagatac aacctgaaag gagaggaggt cttcacgggt    900
cagaccccgg tgaaggcaat aggagccacc gatcagcact ctcagataca gctttacaac    960
gagggcccaa acgacaaagt gataacgttt ttgcggttgg aaaacttcga tagagagatc   1020
ataataccgg acaccggaag agaagagctc aaataccttg caagaaaaag actctctgaa   1080
cttctccttg cagaacagac aggaacagag gaagccctaa ggaaaaacga cagaccgaac   1140
atgaaggtga tcttcgacag actcacctct tacaatgtgg ccagttctt cgcttattat   1200 gaagccgcaa ctgctttcat ggggtatctc ctcgagatca acccgtttga tcagccgggt   1260
gtggaacttg aaagaagat cacgtttgcc ctcatgggaa gggaaggtta cgaatacgaa   1320
ataaaagatc gcaccaagaa ggtgatcata gaatga                             1356
```

<210> SEQ ID NO 11
<211> LENGTH: 471
<212> TYPE: PRT
<213> ORGANISM: Artificial Sequence
<220> FEATURE:
<223> OTHER INFORMATION: Phosphoglucomutase derived from Thermotoga neapolitana (CT2)

<400> SEQUENCE: 11

```
Met Ile Leu Phe Gly Thr Gly Gly Ile Arg Gly Val Met Arg Lys Gly
1               5                   10                  15

Glu Phe Asp Glu Asp Thr Val Lys Arg Ala Ser Leu Ser Val Ala Phe
            20                  25                  30

Trp Met Lys Gln Arg Lys Leu Lys Ser Val Val Ile Ala Tyr Asp Thr
        35                  40                  45

Arg Lys Asn Ser Arg Glu Phe Ala Glu Leu Ala Gly Arg Val Phe Ala
    50                  55                  60

Gly Glu Gly Ile Glu Ala Tyr Val Phe Pro Glu Pro Thr Pro Thr Pro
65                  70                  75                  80

Val Leu Ser Phe Ala Val Arg His Met Lys Ala Gly Ala Gly Val Val
                85                  90                  95

Ile Thr Ala Ser His Asn Pro Pro Glu Tyr Asn Gly Tyr Lys Val Tyr
            100                 105                 110

Thr Trp Asp Gly Val Gln Ala Ile Pro Glu Tyr Thr Asp Glu Ile Thr
        115                 120                 125

Glu Ile Tyr Lys Lys Val Asp Ile Ser Gly Val Arg Glu Gly Gly Phe
    130                 135                 140

Lys His Val Pro Ser Glu Val Lys Glu Ser Tyr Ile Glu Lys Val Val
145                 150                 155                 160

Glu Ile Val Ser Asn Leu Pro Arg Arg Thr Asp Leu Asp Val Ala Tyr
                165                 170                 175

Ser Pro Leu His Gly Thr Gly Ala Asn Tyr Val Pro Glu Val Leu Arg
            180                 185                 190

Arg Leu Gly Phe Lys Val Arg Pro Val Glu Glu Gln Met Lys Pro Asp
        195                 200                 205
```

Pro Asn Phe Ser Thr Val Pro Thr Pro Asn Pro Glu Glu Asp Glu Ala
                 210                 215                 220

Leu Val Leu Leu Asn Lys Lys Glu Ala Thr Leu Gly Leu Ala Thr Asp
225                 230                 235                 240

Pro Asp Cys Asp Arg Val Gly Val Val Tyr Arg Gly Arg Arg Leu Thr
                245                 250                 255

Gly Asn Gln Val Gly Val Leu Leu Thr Asp Phe Leu Leu Glu His Val
                260                 265                 270

Lys Val Glu Asn Pro Leu Val Ile Lys Thr Ile Val Thr Thr Asp Met
                275                 280                 285

Val Arg Pro Ile Cys Glu Glu Arg Gly Ala Tyr Leu Glu Glu Thr Pro
290                 295                 300

Thr Gly Phe Lys Phe Ile Gly His Leu Ile Glu Glu His Thr Lys Lys
305                 310                 315                 320

Gly Asp Arg Asn Phe Val Phe Gly Phe Glu Glu Ser Cys Gly Tyr Leu
                325                 330                 335

Ala Gly Asp His Ala Arg Asp Lys Asp Gly Val Val Gly Ser Val Leu
                340                 345                 350

Ser Ala Ile Ala Phe Ser Asn Tyr Asp Pro Tyr Glu Lys Leu Glu Glu
                355                 360                 365

Leu Tyr Arg Lys Tyr Gly Tyr Tyr Met Glu Lys Leu Ile Asn Phe Lys
370                 375                 380

Phe Glu Asp Val Ser Lys Ala Ile Glu Ile Tyr Asn Ser Leu Lys Glu
385                 390                 395                 400

Tyr Asp Gly Ile Ile Asp Tyr Ser Arg Gly Tyr Lys Gly Ile Ile Pro
                405                 410                 415

Asn Glu Thr Ile Ala Phe Val Phe Glu Lys Ser Arg Ile Phe Val Arg
                420                 425                 430

Pro Ser Gly Thr Glu Pro Lys Leu Lys Val Tyr Ile His Val Arg Gly
                435                 440                 445

Asp Thr Arg Glu Glu Ser Glu Asn Leu Met Lys Glu Ser Glu Arg Lys
                450                 455                 460

Ile Arg Glu Ile Leu Lys Leu
465                 470

<210> SEQ ID NO 12
<211> LENGTH: 1416
<212> TYPE: DNA
<213> ORGANISM: Artificial Sequence
<220> FEATURE:
<223> OTHER INFORMATION: DNA sequence of phosphoglucomutase derived from
      Thermotoga neapolitana (CT2)

<400> SEQUENCE: 12
atgatcctgt ttggaacggg tggaattcga ggtgtgatga gaaagggaga gttcgatgag        60
gacacggtga gagggcttc actgagcgtc gccttctgga tgaaacagag aaaactgaaa       120
agcgttgtga tcgcctacga cacgagaaaa aactccagag agttcgcaga gcttgccgga       180
agggtcttcg caggtgaagg aatagaagcc tacgtgtttc agaaccaac gccaacaccg        240 gttctctctt tcgcagtgag gcacatgaag gccggtgccg tgttgtcat aacagcgagt        300 cacaatcctc cagaatacaa cggatacaag gtttacacct gggatggcgt tcaggcaata       360
ccagagtaca cggacgagat caccgaaata tacaaaaagg tcgatatctc cggagtgagg       420
gagggaggtt caaacacgt accttccgag gtgaaggaga gttacataga aaagtggtt        480 gagatagtct cgaaccttcc aagaagaacg gaccttgacg ttgcctactc tccactccat       540

```
ggaacgggag caaactatgt tccggaggtt ttgagaagac tcggtttcaa agtgagacct    600
gtggaagaac agatgaaacc cgatccaaac ttctccacag tcccaactcc aaatcccgaa    660
gaagatgaag cgctcgtttt gctgaacaaa aggaagcga cccttggact tgcaaccgac     720
ccggactgcg acagggtggg agtggtgtac agaggaagaa ggctcacagg aaaccaggtt    780
ggagtgctcc ttacggactt tctcctcgaa cacgtgaagg tagaaaaccc tctcgtgata    840
aaaacgatcg tcaccacgga catggtgagg cccatctgtg aggaagggg tgcctatctc     900 gaagaaacac aacaggtttt caaattcatc ggtcatttga tagaagaaca cacaaagaaa    960
ggtgacagaa acttcgtctt tggtttcgag gaaagctgtg gatacctcgc aggagaccac   1020
gcaagggaca agatggtgt tgtgggaagt gtcctctctg cgatagcctt cagcaactac    1080
gacccgtacg aaaaactcga gaactctac agaaagtacg ttactacat ggaaaaactc     1140 atcaacttca gttcgaaga cgtcagcaaa gcgatagaaa tatacaactc cctgaaagag   1200
tacgatggaa taatcgatta ctccagaggt tacaaaggaa taattccaaa cgaaaccata   1260
gccttcgtgt tcgaaaaatc cagaatcttc gtcagaccat ctggaacaga accgaagctc   1320
aaggtgtaca tccacgtgag aggggacaca agggaagagt cagagaatct gatgaaggaa   1380
agtgaaagaa agatcaggga gatcctgaaa ctgtga                             1416
```

<210> SEQ ID NO 13
<211> LENGTH: 270
<212> TYPE: PRT
<213> ORGANISM: Artificial Sequence
<220> FEATURE:
<223> OTHER INFORMATION: Polyphosphate-dependent glucokinase CJ_dg_ppgk

<400> SEQUENCE: 13

```
Met Leu Ala Ala Ser Asp Ser Ser Gln His Gly Gly Lys Ala Val Thr
1               5                   10                  15

Leu Ser Pro Met Ser Val Ile Leu Gly Ile Asp Ile Gly Gly Ser Gly
                20                  25                  30

Ile Lys Gly Ala Pro Val Asp Thr Ala Thr Gly Lys Leu Val Ala Glu
            35                  40                  45

Arg His Arg Ile Pro Thr Pro Glu Gly Ala His Pro Asp Ala Val Lys
        50                  55                  60

Asp Val Val Glu Leu Val Arg His Phe Gly His Ala Gly Pro Val
65                  70                  75                  80

Gly Ile Thr Phe Pro Gly Ile Val Gln His Gly His Thr Leu Ser Ala
                85                  90                  95

Ala Asn Val Asp Lys Ala Trp Ile Gly Leu Asp Ala Asp Thr Leu Phe
            100                 105                 110

Thr Glu Ala Thr Gly Arg Asp Val Thr Val Ile Asn Asp Ala Asp Ala
        115                 120                 125

Ala Gly Leu Ala Glu Ala Arg Phe Gly Ala Gly Ala Val Pro Gly
    130                 135                 140

Glu Val Leu Leu Leu Thr Phe Gly Thr Gly Ile Gly Ser Ala Leu Ile
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
        195                 200                 205
```

```
Leu Gln Tyr Leu Glu Gly Leu Phe Ser Pro Asp Leu Phe Ile Ile Gly
            210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp
            260                 265                 270
```

<210> SEQ ID NO 14
<211> LENGTH: 813
<212> TYPE: DNA
<213> ORGANISM: Artificial Sequence
<220> FEATURE:
<223> OTHER INFORMATION: DNA sequence of polyphosphate-dependent glucokinase CJ_dg_ppgk

<400> SEQUENCE: 14

```
atgctggcag ccagtgacag cagccagcat ggcgggaagg ctgttacgct atctcccatg    60
agcgtgatcc tcgggattga cataggtggg agcggcatca agggggcccc tgtggacacg   120
gcaaccggga agctggtggc cgagcgccac cgcatcccca cgcccgaggg cgcgcaccca   180
gacgcggtga aggacgtggt ggttgagctg gtgcggcatt tgggcatgc ggggccagtc    240
ggcatcactt tccctggcat cgtgcagcac ggccataccc tgagcgcagc caatgtggat   300
aaagcctgga ttggcctgga cgccgacacg cttttactg aggcgaccgg tcgcgacgtg    360
accgtgatca cgacgcaga tgccgcgggg ctagcggagg cgaggttcgg ggccggggca   420
ggtgtgccgg gcgaggtgtt gctgttgacc tttgggacag gcatcggcag cgcgctgatc   480
tataacggcg tgctggtgcc caacaccgag tttgggcatc tgtatctcaa gggcgacaag   540
cacgccgaga catgggcgtc cgaccgggcc cgtgagcagg gcgacctgaa ctggaagcag   600
tgggccaaac gggtcagccg gtacctccag tatctggaag gtctcttcag tcccgatctc   660
tttatcatcg gtggggcgt gagcaagaag gccgacaagt ggcagccgca cgtcgcaaca   720
acacgtaccc gcctggtgcc cgctgccctc cagaacgagg ccggaatcgt gggggccgcg   780
atggtggcgg cgcagcggtc acaggggac taa                                813
```

<210> SEQ ID NO 15
<211> LENGTH: 253
<212> TYPE: PRT
<213> ORGANISM: Artificial Sequence
<220> FEATURE:
<223> OTHER INFORMATION: Polyphosphate-dependent glucokinase CJ_at_ppgk

<400> SEQUENCE: 15

```
Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95
```

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190

Leu Glu Arg Leu Glu Ala Leu Phe Trp Pro Asp Leu Phe Ile Leu Gly
        195                 200                 205

Gly Gly Ala Val Lys Asn His Glu Lys Phe Phe Pro Tyr Leu Lys Leu
    210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
                245                 250

<210> SEQ ID NO 16
<211> LENGTH: 762
<212> TYPE: DNA
<213> ORGANISM: Artificial Sequence
<220> FEATURE:
<223> OTHER INFORMATION: DNA sequence of polyphosphate-dependent
      glucokinase CJ at ppgk

<400> SEQUENCE: 16
atggggaggc agggcatgga aattttaggg attgatatcg gaggatccgg catcaaaggg      60
gctccggtgg atgtagaaac cggccagtta accgccgagc gataccgctt acccacccc     120 gaaaatgcct acctgaaga agtggctctg gtagttgccc aaattgtcga cactttcag     180 tggaaaggtc gtgtagggc aggatttcct gctgccatca gcacggcgt ggcacagacg      240 gccgcaaaca tccaccctac atggattgga cttcatgctg caaccttttt cagcgaaaaa     300
tgcggatgtc ctgtctcagt gttgaatgat gcggatgctg ccggactggc ggaaatgatc     360 tttgggcag gaaaaggcca gaaggggtg gtgctgatga ttaccattgg cactggcatc       420
gggacagccc tgttcaccga tgggatattg gtccctaata ccgagttggg acatattgaa     480
attcggggca agatgccga acagcgctct tcggaagccg cccgccagcg gaaggattgg      540
acctggcaac aatgggcaaa gcgtctgaat gagcatttgg agcgcctgga agccctgttc     600
tggcccgatt tattcatcct tggtggaggg gcagtaaaaa atcatgaaaa gttcttccct     660
tatctaaaac tgcgtactcc ctttgttgca gcaaaattgg gaatctggc tgggattgta      720 ggcgcagcgt ggtatgctca cacccaggaa acgcaagcct ga                       762

<210> SEQ ID NO 17
<211> LENGTH: 823
<212> TYPE: PRT
<213> ORGANISM: Artificial Sequence
<220> FEATURE:
<223> OTHER INFORMATION: a-glucanphosphorylase derived from Thermotoga
      neapolitana (CT1)

<400> SEQUENCE: 17

-continued

```
Met Leu Lys Lys Leu Pro Glu Asn Leu Glu His Leu Glu Glu Leu Ala
1               5                   10                  15

Tyr Asn Leu Trp Trp Ser Trp Ser Arg Pro Ala Gln Arg Leu Trp Arg
            20                  25                  30

Lys Ile Asp Pro Glu Gly Trp Glu His Arg Asn Pro Val Lys Ile
        35                  40                  45

Leu Lys Glu Val Ser Asp Glu Arg Leu Glu Glu Leu Ser Lys Asp Asp
50                  55                  60

Asp Phe Ile Ser Leu Tyr Glu Leu Thr Ile Glu Arg Phe Lys Asp Tyr
65                  70                  75                  80

Met Glu Lys Glu Asp Thr Trp Phe Asn Val Asn Tyr Pro Glu Trp Asp
                85                  90                  95

Glu Lys Ile Val Tyr Met Cys Met Glu Tyr Gly Leu Thr Lys Ala Leu
            100                 105                 110

Pro Ile Tyr Ser Gly Gly Leu Gly Ile Leu Ala Gly Asp His Leu Lys
        115                 120                 125

Ser Ala Ser Asp Leu Gly Leu Pro Leu Ile Ala Ile Gly Leu Leu Tyr
130                 135                 140

Lys His Gly Tyr Phe Thr Gln Gln Ile Asp Arg Asp Gly Lys Gln Ile
145                 150                 155                 160

Glu Ile Phe Pro Asp Tyr Asn Pro Glu Asp Leu Pro Met Lys Pro Leu
                165                 170                 175

Lys Asp Glu Lys Gly Asn Gln Val Ile Val Glu Val Pro Leu Asp Ser
            180                 185                 190

Thr Val Val Lys Ala Arg Val Phe Glu Val Lys Val Gly Arg Val Ser
        195                 200                 205

Leu Tyr Leu Leu Asp Pro Asp Ile Glu Glu Asn Glu Glu Arg Tyr Arg
210                 215                 220

Lys Ile Cys Asn Tyr Leu Tyr Asn Pro Glu Pro Asp Val Arg Val Ser
225                 230                 235                 240

Gln Glu Ile Leu Leu Gly Ile Gly Gly Met Lys Leu Leu Arg Ala Leu
                245                 250                 255

Asn Leu Lys Pro Gly Val Ile His Leu Asn Glu Gly His Pro Ala Phe
            260                 265                 270

Ser Ser Leu Glu Arg Ile Lys Asn Tyr Met Glu Glu Gly Tyr Ser Phe
        275                 280                 285

Thr Glu Ala Leu Glu Ile Val Arg Gln Thr Ser Val Phe Thr Thr His
290                 295                 300

Thr Pro Val Pro Ala Gly His Asp Arg Phe Pro Phe Asp Leu Val Glu
305                 310                 315                 320

Lys Lys Leu Ser Lys Phe Phe Glu Gly Phe Glu Lys Arg Asn Leu Leu
                325                 330                 335

Met Asp Leu Gly Lys Asp Glu Thr Gly Ser Phe Asn Met Thr Tyr Leu
            340                 345                 350

Ala Leu Arg Thr Ser Ser Phe Ile Asn Gly Val Ser Lys Leu His Ala
        355                 360                 365

Glu Val Ser Arg Arg Met Phe Lys Asn Val Trp Gln Gly Val Pro Val
370                 375                 380

Glu Glu Ile Pro Ile Glu Gly Ile Thr Asn Gly Val His Met Gly Thr
385                 390                 395                 400

Trp Ile Asn Arg Glu Met Arg Lys Leu Tyr Asp Arg Tyr Leu Gly Arg
                405                 410                 415

Val Trp Arg Asp His Thr Asp Leu Glu Gly Ile Trp Tyr Gly Val Asp
```

```
                420                 425                 430
Arg Ile Pro Asp Glu Leu Trp Gln Ala His Leu Arg Ala Lys Lys
            435                 440                 445
Arg Phe Ile Glu Tyr Ile Lys Glu Ser Val Arg Arg Asn Glu Arg
            450                 455                 460
Leu Gly Ile Asp Glu Asp Val Pro Asn Ile Asp Glu Asn Ser Leu Ile
465                 470                 475                 480
Ile Gly Phe Ala Arg Arg Phe Ala Thr Tyr Lys Arg Ala Val Leu Leu
                485                 490                 495
Leu Ser Asp Leu Glu Arg Leu Lys Lys Ile Leu Asn Asp Pro Glu Arg
            500                 505                 510
Pro Val Tyr Val Val Tyr Ala Gly Lys Ala His Pro Arg Asp Asp Ala
            515                 520                 525
Gly Lys Glu Phe Leu Lys Arg Ile Tyr Glu Val Ser Gln Met Pro Glu
            530                 535                 540
Phe Lys Asn Arg Ile Ile Val Leu Glu Asn Tyr Asp Ile Gly Met Ala
545                 550                 555                 560
Arg Leu Met Val Ser Gly Val Asp Val Trp Leu Asn Asn Pro Arg Arg
                565                 570                 575
Pro Met Glu Ala Ser Gly Thr Ser Gly Met Lys Ala Ala Asn Gly
            580                 585                 590
Val Leu Asn Ala Ser Val Tyr Asp Gly Trp Trp Val Glu Gly Tyr Asn
            595                 600                 605
Gly Arg Asn Gly Trp Val Ile Gly Asp Glu Ser Val Leu Pro Glu Thr
            610                 615                 620
Glu Val Asp Asp Pro Arg Asp Ala Glu Ala Leu Tyr Asp Leu Leu Glu
625                 630                 635                 640
Asn Glu Ile Ile Pro Thr Tyr Tyr Glu Asn Lys Glu Lys Trp Ile Phe
                645                 650                 655
Met Met Lys Glu Ser Ile Lys Ser Val Ala Pro Arg Phe Ser Thr Thr
                660                 665                 670
Arg Met Leu Lys Glu Tyr Thr Glu Lys Phe Tyr Ile Lys Gly Leu Val
            675                 680                 685
Asn Lys Glu Trp Leu Glu Arg Lys Glu Asn Ala Glu Arg Phe Gly Ala
            690                 695                 700
Trp Lys Glu Arg Ile Leu Arg Asn Trp Ser Ser Val Ser Ile Glu Arg
705                 710                 715                 720
Ile Val Leu Glu Asp Thr Arg Ser Val Glu Val Thr Val Lys Leu Gly
                725                 730                 735
Asp Leu Ser Pro Asp Asp Val Leu Val Glu Leu Leu Ile Gly Arg Gly
            740                 745                 750
Glu Ser Met Glu Asp Leu Glu Ile Trp Lys Val Ile Gln Ile Arg Lys
            755                 760                 765
His Arg Arg Glu Gly Asp Leu Phe Ile Tyr Ser Tyr Val Asn Gly Ala
            770                 775                 780
Leu Gly His Leu Gly Ser Pro Gly Trp Phe Tyr Ala Val Arg Val Leu
785                 790                 795                 800
Pro Tyr His Pro Lys Leu Pro Thr Arg Phe Leu Pro Glu Ile Pro Val
                805                 810                 815
Val Trp Lys Lys Val Leu Gly
            820

<210> SEQ ID NO 18
```

<211> LENGTH: 2472
<212> TYPE: DNA
<213> ORGANISM: Artificial Sequence
<220> FEATURE:
<223> OTHER INFORMATION: DNA sequence of a-glucanphosphorylase derived from Thermotoga neapolitana (CT1)

<400> SEQUENCE: 18

| | | | | | |
|---|---|---|---|---|---|
| atgctgaaga | aactcccgga | gaatctggag | catctggaag | aactcgccta | caacctctgg | 60 |
| tggagctggt | ctaggcccgc | tcagagactc | tggagaaaga | tagatccgga | aggctgggag | 120 |
| gaacacagaa | accccgttaa | atactgaaa | gaagtttctg | atgaaaggct | cgaagaactt | 180 |
| tcaaaagatg | atgatttcat | atccctctac | gaactcacca | ttgaaaggtt | caaggattac | 240 |
| atggagaaag | aagacacctg | gttcaacgtg | aactaccccg | aatgggacga | aagatcgtc | 300 |
| tacatgtgta | tggagtacgg | tttgaccaaa | gcccttccga | tctactccgg | tggtcttgga | 360 |
| atcctcgcgg | gagaccatct | caaatccgca | agcgatcttg | gacttcctct | catagcgatc | 420 |
| ggacttctct | acaaacatgg | atatttcacc | cagcagatcg | acagagatgg | aaaacagata | 480 |
| gagattttcc | ctgattacaa | cccagaggac | ttacccatga | agcccctgaa | ggatgaaaag | 540 |
| ggaaaccagg | tgatcgtgga | ggttcctctc | gacagtaccg | tggtgaaggc | acgtgttttt | 600 |
| gaagtgaagg | taggaagggt | gagtctgtac | ctgctcgatc | cggacatcga | ggaaaacgag | 660 |
| gaacgataca | gaaagatctg | caactaccttt | tacaacccgg | aacccgatgt | gagggtctcc | 720 |
| caggagatac | tcctcggaat | tgggggaatg | aagcttctca | gggctctgaa | cctgaaacca | 780 |
| ggagtcatcc | atctgaacga | aggacatccg | gcgttctctt | ccctgaaag | gataaagaac | 840 |
| tacatggaag | aaggatattc | cttcacagag | gcccttgaga | tcgtgagaca | gacgagtgtg | 900 |
| tttacaaccc | acacacccgt | tcccgctgga | cacgacagat | ttcccttga | cctcgtggaa | 960 |
| aagaaacttt | cgaaattctt | cgaaggattc | gaaaagagaa | atcttctcat | ggatcttggg | 1020 |
| aaagatgaaa | caggcagttt | caacatgacg | tatcttgccc | tgagaacgtc | ctcttcata | 1080 |
| aacggcgtga | gcaaactgca | tgcggaagtt | tccagaagga | tgttcaaaaa | cgtgtggcag | 1140 |
| ggtgttcccg | tggaggaaat | accgatcgaa | gggataacga | acggcgttca | catgggaacc | 1200 |
| tggatcaacc | gtgagatgag | aaaactgtac | gacagatatc | tcggaagggt | atggagagat | 1260 |
| cacaccgacc | ttgagggtat | ctggtacggt | gttgacagga | ttccagatga | agaactctgg | 1320 |
| caggctcacc | tgagggcaaa | gaagagattc | atcgagtaca | aaaagaatc | ggtaagaaga | 1380 |
| agaaacgaga | gactgggaat | cgacgaagat | gtgccgaaca | tcgatgaaaa | ttcgctcatc | 1440 |
| ataggttttg | caagaaggtt | tgccacttac | aagagggcag | ttctcctgct | cagcgatctg | 1500 |
| gagagactca | agaagatcct | caacgatcca | gaaagacccg | tttacgtggt | ctatgcgggg | 1560 |
| aaggcccatc | aagggacga | tgcggggaag | gaatttttga | aacgcatcta | cgaagtctcg | 1620 |
| cagatgcctg | agttcaaaaa | caggatcatc | gtactggaaa | actacgacat | tggaatggca | 1680 |
| cggctcatgg | tgtcgggagt | ggatgtgtgg | ctgaacaacc | cgagaagacc | catgaagca | 1740 |
| agtggaacaa | gcggaatgaa | ggcagcagcc | aacggagttc | ttaacgcgag | tgtttacgat | 1800 |
| ggatggtggg | ttgaagggta | caacggcaga | acggctgggt | catagggcga | tgaaagcgtt | 1860 |
| cttccagaga | cggaagtgga | cgatcccagg | gacgcagaag | cactctacga | tctcctcgaa | 1920 |
| aacgaaatca | tcccaaccta | ctacgaaaac | aaagaaaagt | ggatcttcat | gatgaaagag | 1980 |
| agcataaaga | gtgttgctcc | aagattcagc | accaccagaa | tgctcaaaga | atacacggag | 2040 |
| aagttctaca | taagggact | tgtgaacaaa | gaatggcttg | aaagaaaaga | aaacgccgaa | 2100 |

```
aggtttggtg catggaagga aaggatcctc agaaactgga gcagcgtttc catagaaaga    2160
atcgtccttg aggacacaag gagtgttgag gtgacggtga aactgggaga cctttcacct    2220
gatgatgtac tggttgaact tttgattgga agaggagaaa gcatggaaga tctggagatc    2280
tggaaggtga tacagataag aaagcacaga agggaagggg atctgttcat ctacagttat    2340
gtcaacggtg ccctcggtca tcttggctct ccgggatggt tctacgcggt gagggtgcta    2400
ccttatcatc cgaaacttcc caccagattc ttgccggaga tacctgtggt gtggaaaaag    2460
gttctcgggt ga                                                         2472
```

```
<210> SEQ ID NO 19
<211> LENGTH: 441
<212> TYPE: PRT
<213> ORGANISM: Artificial Sequence
<220> FEATURE:
<223> OTHER INFORMATION: 4-a-glucanotransferase derived from Thermotoga
      maritima(TN2)

<400> SEQUENCE: 19
```

Met Ile Gly Tyr Gln Ile Tyr Val Arg Ser Phe Arg Asp Gly Asn Phe
1               5                   10                  15

Asp Gly Val Gly Asp Phe Lys Gly Leu Lys Gly Ala Ile Ser Tyr Leu
            20                  25                  30

Lys Glu Leu Gly Val Asp Phe Val Trp Leu Met Pro Val Phe Ser Ser
        35                  40                  45

Ile Ser Phe His Gly Tyr Asp Val Asp Phe Tyr Ser Phe Lys Ala
    50                  55                  60

Glu Tyr Gly Asp Glu Lys Asp Phe Arg Glu Met Ile Glu Ala Phe His
65                  70                  75                  80

Asp Asn Gly Ile Lys Val Val Leu Asp Leu Pro Ile His His Thr Gly
                85                  90                  95

Phe Leu His Val Trp Phe Gln Lys Ala Leu Lys Gly Asp Pro His Tyr
            100                 105                 110

Arg Asp Tyr Tyr Val Trp Ala Ser Glu Lys Thr Asp Leu Asp Glu Arg
        115                 120                 125

Arg Glu Trp Asp Asn Glu Arg Ile Trp His Pro Leu Glu Asp Gly Arg
    130                 135                 140

Phe Tyr Arg Gly Leu Phe Gly Pro Leu Ser Pro Asp Leu Asn Tyr Asp
145                 150                 155                 160

Asn Pro Gln Val Phe Glu Glu Met Lys Lys Val Val Tyr His Leu Leu
                165                 170                 175

Glu Met Gly Val Asp Gly Phe Arg Phe Asp Ala Ala Lys His Met Arg
            180                 185                 190

Asp Thr Leu Glu Gln Asn Val Arg Phe Trp Arg Tyr Phe Leu Ser Asp
        195                 200                 205

Ile Glu Gly Ile Phe Leu Ala Glu Ile Trp Ala Glu Ser Lys Val Val
    210                 215                 220

Asp Glu His Gly Arg Ile Phe Gly Tyr Met Leu Asn Phe Asp Thr Ser
225                 230                 235                 240

His Cys Ile Lys Glu Ala Val Trp Lys Glu Asn Phe Lys Val Leu Ile
                245                 250                 255

Glu Ser Ile Glu Arg Ala Leu Val Gly Lys Asp Tyr Leu Pro Val Asn
            260                 265                 270

Phe Thr Ser Asn His Asp Met Ser Arg Leu Ala Ser Phe Glu Gly Gly
        275                 280                 285

```
Leu Ser Glu Glu Lys Val Lys Leu Ser Leu Ser Ile Leu Phe Thr Leu
    290                 295                 300

Pro Gly Val Pro Leu Ile Phe Tyr Gly Asp Glu Leu Gly Met Lys Gly
305                 310                 315                 320

Ile Tyr Arg Lys Pro Asn Thr Glu Val Val Leu Asp Pro Phe Pro Trp
                325                 330                 335

Ser Glu Asn Met Cys Val Gly Gln Thr Phe Trp Lys Trp Pro Ala
                340                 345                 350

Tyr Asn Asp Pro Phe Ser Gly Val Ser Val Glu Tyr Gln Arg Arg Asn
                355                 360                 365

Arg Asp Ser Ile Leu Ser His Thr Met Arg Trp Ala Gly Phe Arg Gly
    370                 375                 380

Glu Asn His Trp Leu Asp Arg Ala Asn Ile Glu Phe Leu Cys Lys Glu
385                 390                 395                 400

Glu Lys Leu Leu Val Tyr Arg Leu Val Asp Glu Gly Arg Ser Leu Lys
                405                 410                 415

Val Ile His Asn Leu Ser Asn Gly Glu Met Val Phe Glu Gly Val Arg
                420                 425                 430

Val Gln Pro Tyr Ser Thr Glu Val Val
    435                 440

<210> SEQ ID NO 20
<211> LENGTH: 1326
<212> TYPE: DNA
<213> ORGANISM: Artificial Sequence
<220> FEATURE:
<223> OTHER INFORMATION: DNA sequence of 4-a-glucanotransferase derived
      from Thermotoga maritima(TN2)

<400> SEQUENCE: 20
atgataggct accagatcta cgtgagatca ttcagggatg aaacttcga tggtgtgggg      60 gatttcaaag gattgaaagg tgcgatttcc tacctgaaag aactgggtgt tgattttgtc    120
tggctcatgc ccgtcttttc ctccatttcc ttccacgggt atgacgtggt ggatttttat    180
tctttcaaag ccgagtacgg agacgagaaa gactttagag agatgatcga ggcgttccac    240
gacaacggta taaaagtcgt tctcgatctt cccatccatc atactggttt cctccatgtg    300
tggtttcaga agccctgaa aggagatcca cactacaggg attattacgt atgggcgagt    360
gaaaaaacgg atctggacga agaagagag tgggacaacg aaaggatctg gcatcctctg    420
gaggacggaa ggttctacag aggactttc ggtcccctct cacccgatct gaactacgat    480
aacccgcagg tttttgaaga gatgaagaag gtggtttatc accttcttga atgggagtg    540 gacggattca gattcgacgc agcaaagcac atgagagata ctctggaaca gaacgttcgc    600
ttttggaggt atttcctctc cgatattgag ggaatattcc ttgcggaaat ctgggcagaa    660
tccaaagttg tggatgaaca cggcaggata ttcggctaca tgctaaattt cgatacctca    720
cactgtatta aggaagcggt gtggaaggaa aacttcaaag tgttgatcga gtcgatcgaa    780
agggccctgg ttggaaaaga ttatctgccg gtgaacttca tcgaacca tgatatgtca    840 aggcttgcga gtttcgaagg agggttgagt gaagagaagg tgaaactctc acttttccatt    900 ctgttcacgc ttcccgggt tcctctcata ttctacggag cgaactggg aatgaaagga    960 atctatcgaa aaccgaacac ggaagtcgtg ctggatccgt tcccctggag cgaaaacatg   1020
tgtgttgaag gccagacatt ttggaaatgg cccgcgtata cgatccatt ctccggtgtt   1080 tctgttgagt atcagaggag aaatcgtgat tcgattctct cacacacgat gaggtgggca   1140
```

```
ggattcagag gggaaaatca ctggctggac agggcaaaca tcgaatttct gtgcaaagaa    1200
gaaaaactgc tcgtgtacag actggtcgat gaagggcgtt ctctgaaagt gatacacaac    1260
ctgtcgaatg gtgaaatggt gtttgaggga gtgcgcgtac aaccctacag cacggaggtg    1320
gtttga                                                               1326
```

```
<210> SEQ ID NO 21
<211> LENGTH: 34
<212> TYPE: DNA
<213> ORGANISM: Artificial Sequence
<220> FEATURE:
<223> OTHER INFORMATION: Forward primer DNA sequence of CT1

<400> SEQUENCE: 21
aggagaaact catatgctga agaaactccc ggag                                34

<210> SEQ ID NO 22
<211> LENGTH: 21
<212> TYPE: DNA
<213> ORGANISM: Artificial Sequence
<220> FEATURE:
<223> OTHER INFORMATION: Reverse primer DNA sequence of CT1

<400> SEQUENCE: 22 agcccctcg agcccgagaa c                                               21

<210> SEQ ID NO 23
<211> LENGTH: 26
<212> TYPE: DNA
<213> ORGANISM: Artificial Sequence
<220> FEATURE:
<223> OTHER INFORMATION: Forward primer DNA sequence of CT2

<400> SEQUENCE: 23
aaagggcata tgatcctgtt tggaac                                         26

<210> SEQ ID NO 24
<211> LENGTH: 27
<212> TYPE: DNA
<213> ORGANISM: Artificial Sequence
<220> FEATURE:
<223> OTHER INFORMATION: Reverse primer DNA sequence of CT2

<400> SEQUENCE: 24
ataccagtct cgagcagttt caggatc                                        27

<210> SEQ ID NO 25
<211> LENGTH: 34
<212> TYPE: DNA
<213> ORGANISM: Artificial Sequence
<220> FEATURE:
<223> OTHER INFORMATION: Forward primer DNA sequence of TN1

<400> SEQUENCE: 25
ttactgaggg catatgaaaa agatggcttt gaaa                                34

<210> SEQ ID NO 26
<211> LENGTH: 30
<212> TYPE: DNA
<213> ORGANISM: Artificial Sequence
<220> FEATURE:
<223> OTHER INFORMATION: Reverse primer DNA sequence of TN1

<400> SEQUENCE: 26
aagacgcgtc gacttctatg atcaccttct                                     30
```

```
<210> SEQ ID NO 27
<211> LENGTH: 31
<212> TYPE: DNA
<213> ORGANISM: Artificial Sequence
<220> FEATURE:
<223> OTHER INFORMATION: Forward primer DNA sequence of TN2

<400> SEQUENCE: 27
atagagggca tatgataggc taccagatct a                              31

<210> SEQ ID NO 28
<211> LENGTH: 24
<212> TYPE: DNA
<213> ORGANISM: Artificial Sequence
<220> FEATURE:
<223> OTHER INFORMATION: Reverse primer DNA sequence of TN2

<400> SEQUENCE: 28
atcttcatct cgagaaccac ctcc                                      24

<210> SEQ ID NO 29
<211> LENGTH: 28
<212> TYPE: DNA
<213> ORGANISM: Artificial Sequence
<220> FEATURE:
<223> OTHER INFORMATION: Forward primer DNA sequence of T4

<400> SEQUENCE: 29
ttttcatatg gagggaggga tcgaattg                                  28

<210> SEQ ID NO 30
<211> LENGTH: 27
<212> TYPE: DNA
<213> ORGANISM: Artificial Sequence
<220> FEATURE:
<223> OTHER INFORMATION: Reverse primer DNA sequence of T4

<400> SEQUENCE: 30
catactcgag cttcccctct cctatct                                   27
```